US009975923B2

United States Patent

(12) United States Patent
Baric et al.

(10) Patent No.: US 9,975,923 B2
(45) Date of Patent: May 22, 2018

(54) METHODS AND COMPOSITIONS FOR NOROVIRUS BLOCKADE EPITOPES

(71) Applicant: The University of North Carolina at Chapel Hill, Chapel Hill, NC (US)

(72) Inventors: Ralph Steven Baric, Haw River, NC (US); Lisa Chon Lindesmith, Apex, NC (US); Kari Moore Debbink, Durham, NC (US); Eric Francis Donaldson, Durham, NC (US); Jesica Anne Swanstrom, Morrisville, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 127 days.

(21) Appl. No.: 14/213,469

(22) Filed: Mar. 14, 2014

(65) Prior Publication Data

US 2014/0271712 A1 Sep. 18, 2014

Related U.S. Application Data

(60) Provisional application No. 61/798,946, filed on Mar. 15, 2013.

(51) Int. Cl.

| | |
|---|---|
| ***A61K 39/12*** | (2006.01) |
| ***A61K 39/00*** | (2006.01) |
| ***C07K 14/005*** | (2006.01) |
| ***G01N 33/569*** | (2006.01) |

(52) U.S. Cl.

CPC ..... *C07K 14/005* (2013.01); *G01N 33/56983* (2013.01); *C12N 2770/16022* (2013.01); *C12N 2770/16034* (2013.01); *C12N 2770/36143* (2013.01); *G01N 2333/08* (2013.01)

(58) Field of Classification Search

None

See application file for complete search history.

(56) References Cited

U.S. PATENT DOCUMENTS

2009/0054246 A1* 2/2009 Peabody et al. .................. 506/7
2012/0156243 A1 6/2012 Richardson et al.

(Continued)

FOREIGN PATENT DOCUMENTS

WO WO 2007081447 A2 * 7/2007 ............ A61K 39/12
WO WO 2012/006293 A1 1/2012

OTHER PUBLICATIONS

Bok et al., "Evolutionary Dynamic of GII.4 Noroviruses over a 34-Year Period," Journal of Virology, vol. 83, No. 22: 11890-11901 (2009).*

(Continued)

*Primary Examiner* — Janet L Andres
*Assistant Examiner* — M Franco G Salvoza
(74) *Attorney, Agent, or Firm* — Myers Bigel, P.A.

(57) ABSTRACT

The present invention provides methods and compositions comprising a chimeric norovirus capsid protein comprising a norovirus VP1 major capsid protein backbone comprising a norovirus epitope selected from the group consisting of: a) Epitope A; b) Epitope B; c) Epitope C; d) Epitope D; e) Epitope E; f) Epitope F; and g) any combination of (a) through (f) above, wherein the norovirus epitope is from a norovirus strain that is different from the norovirus VP1 major capsid protein backbone.

8 Claims, 13 Drawing Sheets

A)

| Epitope | A | | | | | | B | | C | | D | | E | | | F | | | |
|---|---|---|---|---|---|---|---|---|---|---|---|---|---|---|---|---|---|---|---|
| Amino Acids | 294 | 296 | 297 | 298 | 368 | 372 | 333 | 382 | 340 | 376 | 393 | 394 | 406 | 411 | 412 | 310 | 316 | 483 | 492 |
| GII.4.1974 (SEQ ID NO:14) | G | S | H | D | T | N | L | K | A | Q | D | H | N | S | G | N | E | R | K |
| GII.4.1987 (SEQ ID NO:2) | V | S | H | D | T | N | L | K | A | Q | D | H | N | T | G | N | E | R | K |
| GII.4.1997 (SEQ ID NO:3) | A | S | H | D | T | N | M | K | E | Q | G | N | N | T | G | N | E | R | K |

B)

| Epitope | A | | | | | | B | | C | | D | | | E | | | F | | | |
|---|---|---|---|---|---|---|---|---|---|---|---|---|---|---|---|---|---|---|---|---|
| Amino Acids | 294 | 296 | 297 | 298 | 368 | 372 | 333 | 382 | 340 | 376 | 393 | 394 | 395 | 407 | 412 | 413 | 310 | 316 | 484 | 493 |
| GII.4.2002 (SEQ ID NO:4) | A | T | H | N | N | N | M | K | G | E | N | G | A | S | T | G | N | E | R | K |
| GII.4.2002a (SEQ ID NO:5) | A | T | H | N | N | N | M | K | G | E | N | G | T | S | T | G | N | E | R | K |
| GII.4.2004 (SEQ ID NO:6) | A | A | Q | N | S | S | V | R | R | E | S | T | T | D | D | S | N | E | R | K |
| GII.4.2005 (SEQ ID NO:7) | P | T | R | T | A | D | M | R | G | E | S | S | A | D | T | V | N | E | R | K |
| GII.4.2006 (SEQ ID NO:8) | A | S | R | N | S | E | V | K | G | E | S | T | T | S | N | V | N | E | R | K |
| GII.4.2007 (SEQ ID NO:9) | A | T | Q | E | S | S | V | R | R | E | S | T | T | N | D | S | N | E | R | K |
| GII.4.2008a (SEQ ID NO:10) | A | S | R | N | A | D | M | K | S | E | S | T | T | N | T | G | N | E | R | K |
| GII.4.2008s (SEQ ID NO:11) | S | S | R | N | A | D | V | K | A | D | N | T | A | S | N | S | S | E | R | K |
| GII.4.2009 (SEQ ID NO:12) | P | S | R | N | A | D | V | K | T | E | S | T | T | S | N | I | S | E | R | K |
| GII.4.2012 (SEQ ID NO:13) | T | S | R | N | E | D | V | K | T | E | G | T | T | S | N | T | D | E | R | K |

(56) References Cited

U.S. PATENT DOCUMENTS

2012/0164155 A1* 6/2012 Grgacic ................. A61K 39/12 424/159.1
2013/0052216 A1 2/2013 Steadman et al.
2013/0171185 A1* 7/2013 Settembre et al. ........ 424/192.1

OTHER PUBLICATIONS

Vega et al., "Novel Surveillance Network for Norovirus Gastroenteritis Outbreaks, United States," Emerging Infectious Diseases, vol. 17, No. 8 (2011).*
Meloen et al., "Mimotopes: realization of an unlikely concept" Journal of Molecular Recognition 13: 352-359 (2000).*
Rudikoff et al., "Single amino acid substitution altering antigen-binding specificity," Proc Natl Acad Sci USA 79:1979-1983 (1982).*
Baric et al. "Expression and Self-Assembly of Norwalk Virus Capsid Protein from Venezuelan Equine Encephalitis Virus Replicons" *Journal of Virology* 76(6):3023-3030 (2002).
Cannon et al. "Herd Immunity to GII.4 Noroviruses Is Supported by Outbreak Patient Sera" *Journal of Virology* 83(11):5363-5374 (2009).
Corti et al. "Broadly Neutralizing Antiviral Antibodies" *Annual Review of Immunology* 31:705-742 (2013).
Debbink et al. "Genetic Mapping of a Highly Variable Norovirus GII.4 Blockade Epitope: Potential Role in Escape from Human Herd Immunity" *Journal of Virology* 86(2):1214-1226 (2012).
Debbink et al. "Norovirus Immunity and the Great Escape" *PLoS Pathogens* 8(10):e1002921 (2012).
Debbink et al. "Emergence of New Pandemic GII.4 Sydney Norovirus Strain Correlates With Escape From Herd Immunity" *Journal of Infectious Diseases* 208:1877-1887 (2013).
Debbink et al. "Chimeric GII.4 Norovirus Virus-Like-Particle-Based Vaccines Induce Broadly Blocking Immune Responses" *Journal of Virology* 88(13):7256-7266 (2014).
Debbink et al. "Human Norovirus Detection and Production, Quantification, and Storage of Virus-Like Particles" *Current Protocols in Microbiology* 31:1-58 (2014).
Debbink et al. "Within-Host Evolution Results in Antigenically Distinct GII.4 Noroviruses" *Journal of Virology* 88(13):7244-7255 (2014).
Eden et al. "Recombination within the Pandemic Norovirus GII.4 Lineage" *Journal of Virology* 87(11):6270-6282 (2013).
GenBank Accession No. AAK50355.1 *capsid protein* [Human calicivirus Hu/NLV/GII/MD145-12/1987/US] Jan. 29, 2002.
GenBank Accession No. AAZ31376.2 *capsid protein* [Norovirus Hu/GII.4/Hunter284E/04O/AU] Sep. 14, 2009.
GenBank Accession No. ACT76139.1 VP1 [Norovirus Hu/GII.4/CHDC5191/1974/US] Nov. 2, 2009.
GenBank Accession No. ACX31885.1 *major capsid protein* [Norovirus Hu/GII.4/Armidale/NSW390I/2008/AU] Feb. 6, 2012.
GenBank Accession No. ADD1037501.1 *major capsid protein* [Norovirus Hu/GII.4/NewOrleans1805/2009/USA] Aug. 18, 2011.
GenBank Accession No. AFJ04707.1 *major capsid protein* [Norovirus Hu/GII.4/1997/USA] May 8, 2012.
GenBank Accession No. AFJ04708.1 *major capsid protein* [Norovirus Hu/GII.4/FarmingtonHills/2004/USA] May 8, 2012.
GenBank Accession No. AFJ04709.1 *major capsid protein* [Norovirus Hu/GII.4/Minerva/2006/USA] May 8, 2012.
GenBank Accession No. AFV08795.1 VP1 [Norovirus Hu/GII.4/Sydney/NSW0514/2012/AU] Oct. 21, 2012.
GenBank Accession No. BAE98194.1 *capsid protein* [Norovirus Hu/Sakai/04-179/2005/JP] Jul. 22, 2006.
GenBank Accession No. BAH30707.1 *capsid protein* [Norovirus Hu/GII.4/Stockholm/19865/2008/SE] Mar. 31, 2009.
GenBank Accession No. BAH56690.1 *capsid protein* [Norovirus Hu/GII.4/cruiseship/2007/ZAF] Apr. 21, 2009.
Hansman et al. "Structural Basis for Broad Detection of Genogroup II Noroviruses by a Monoclonal Antibody That Binds to a Site Occluded in the Viral Particle" *Journal of Virology* 86(7):3635-3646 (2012).
Lindesmith et al. "Norovirus GII.4 Strain Antigenic Variation" *Journal of Virology* 85(1):231-242 (2011).
Lindesmith et al. "Immunogenetic Mechanisms Driving Norovirus GII.4 Antigenic Variation" *PLoS Pathogens* 8(5):e1002705 (2012).
Lindesmith et al. "Emergence of a Norovirus GII.4 Strain Correlates with Changes in Evolving Blockade Epitopes" *Journal of Virology* 87(5):2803-2813 (2013).
Lindesmith et al. "Particle Conformation Regulates Antibody Access to a Conserved GII.4 Norovirus Blockade Epitope" *Journal of Virology* 88(16):8826-8842 (2014).
Lindesmith et al. "Broad Blockade Antibody Responses in Human Volunteers after Immunization with a Multivalent Norovirus VLP Candidate Vaccine: Immunological Analyses from a Phase I Clinical Trial" *PLoS Medicine* 12(3):1-32 (2015).
Meloen et al. "Mimotopes: realization of an unlikely concept" *Journal of Molecular Recognition* 13:352-359 (2000).
Richardson et al. "Norovirus virus-like particle vaccines for the prevention of acute gastroenteritis" *Expert Review of Vaccines* 12(2):155-167 (2013).
Swanstrom et al. "Characterization of Blockade Antibody Responses in GII.2.1976 Snow Mountain Virus-Infected Subjects" *Journal of Virology* 88(2):829-837 (2014).
Tan et al. "Norovirus P Particle, a Novel Platform for Vaccine Development and Antibody Production" *Journal of Virology* 85(2):753-764 (2011).
Van Beek et al. "Indications for worldwide increased norovirus activity associated with emergence of a new variant of genotype II.4, late 2012" *Eurosurveillance* 18(1):1-2 (2013).
Lindesmith L.C. et al. "Monoclonal Antibody-Based Antigenic Mapping of Norovirus GH.4-2002", *J. Virol.* 86(2):873-883 (2012).
International Search Report and Written Opinion Corresponding to International Application No. PCT/US2014/029969; dated Sep. 11, 2014 (12 pages).
Allen et al. "Analysis of Amino Acid Variation in the P2 Domain of the GII-4 Norovirus VP1 Protein Reveals Putative Variant-Specific Epitopes" *PLoS ONE* 3(1):e1485 (2008).
Atmar et al. "Norovirus Vaccine against Experimental Human Norwalk Virus Illness" *The New England Journal of Medicine* 365(23):2178-2187 (2011).
Bull et al. "Emergence of a New Norovirus Genotype II.4 Variant Associated with Global Outbreaks of Gastroenteritis" *Journal of Clinical Microbiology* 44(2):327-333 (2006).
Bull et al. "Rapid Evolution of Pandemic Noroviruses of the GII.4 Lineage" *PLoS Pathogens* 6(3):e1000831 (2010).
Cao et al. "Structural Basis for the Recognition of Blood Group Trisaccharides by Norovirus" *Journal of Virology* 81(11):5949-5957 (2007).
Donaldson et al. "Norovirus pathogenesis: mechanisms of persistence and immune evasion in human populations" *Immunological Reviews* 225:190-211 (2008).
Harrington et al. "Binding of Norwalk Virus-Like Particles to ABH Histo-Blood Group Antigens Is Blocked by Antisera from Infected Human Volunteers or Experimentally Vaccinated Mice" *Journal of Virology* 76(23):12335-12343 (2002).
Lindesmith et al. "Mechanisms of GII.4 Norovirus Persistence in Human Populations" *PLoS Medicine* 5(2):e31 (2008).
Lindesmith et al. "Heterotypic Humoral and Cellular Immune Responses following Norwalk Virus Infection" *Journal of Virology* 84(4):1800-1815 (2010).
Lochridge et al. "Epitopes in the P2 domain of norovirus VP1 recognized by monocloncal antibodies that block cell interactions" *Journal of General Virology* 86:2799-2806 (2005).
Noel et al. "Identification of a Distinct Common Strain of 'Norwalk-like Viruses' Having a Global Distribution" *The Journal of Infectious Diseases* 179:1334-1344 (1999).
Okada et al. "Genetic analysis of noroviruses associated with fatalities in healthcare facilities" *Archives of Virology* 151:1635-1641 (2006).

(56) References Cited

OTHER PUBLICATIONS

Phan et al. "Changing Distribution of Norovirus Genotypes and Genetic Analysis of Recombinant GIIb Among Infants and Children With Diarrhea in Japan" *Journal of Medical Virology* 78:971-978 (2006).

Schorn et al. "Chronic Norovirus Infection after Kidney Transplantation: Molecular Evidence for Immune-Driven Viral Evolution" *Clinical Infectious Diseases* 51(3):307-314 (2010).

Siebenga et al. "Epochal Evolution of GGII.4 Norovirus Capsid Proteins from 1995 to 2006" *Journal of Virology* 81(18):9932-9941 (2007).

Siebenga et al. "Phylodynamic Reconstruction Reveals Norovirus GII.4 Epidemic Expansions and their Molecular Determinants" *PLoS Pathogens* 6(5):e1000884 (2010).

Vega et al. "Novel Surveillance Network for Norovirus Gastroenteritis Outbreaks, United States" *Emerging Infectious Diseases* 17(8):1389-1395 (2011).

Vinje et al. "The Incidence and Genetic Variability of Small Round-Structured Viruses in Outbreaks of Gastroenteritis in The Netherlands" *The Journal of Infectious Diseases* 176:1374-1378 (1997).

Widdowson et al. "Outbreaks of Acute Gastroenteritis on Cruise Ships and on Land: Identification of a Predominant Circulating Strain of Norovirus—United States, 2002" *The Journal of Infectious Diseases* 190:27-36 (2004).

International Preliminary Report on Patentability corresponding to International Patent Application No. PCT/US2014/029969 (8 pages) (dated Sep. 15, 2015).

Green et al. "A Predominant Role for Norwalk-like Viruses as Agents of Epidemic Gastroenteritis in Maryland Nursing Homes for the Elderly" *The Journal of Infectious Diseases* 185(2):133-146 (2002).

Partial Supplementary European Search Report (Rule 164(1) EPC) corresponding to European Patent Application No. 14764479.3 (9 pages) (dated Oct. 26, 2016).

Zheng et al. "Norovirus classification and proposed strain nomenclature" *Virology* 346:312-323 (2006).

Dingle et al. "Mutation in a Lordsdale Norovirus Epidemic Strain as a Potential Indicator of Transmission Routes" *Journal of Clinical Microbiology* 42(9):3950-3957 (2004).

Extended European Search Report corresponding to European Patent Application No. 14764479.3 (15 pages) (dated Feb. 28, 2017).

Kim et al. "Virus-like Particles Containing Multiple M2 Extracellular Domains Confer Improved Cross-protection Against Various Subtypes of Influenza Virus" *Molecular Therapy* 21(2):485-492 (2013).

* cited by examiner

A)

| Epitope | A | | | | | | B | | C | | D | | E | | | F | | | |
|---|---|---|---|---|---|---|---|---|---|---|---|---|---|---|---|---|---|---|---|
| Amino Acids | 294 | 296 | 297 | 298 | 368 | 372 | 333 | 382 | 340 | 376 | 393 | 394 | 406 | 411 | 412 | 310 | 316 | 483 | 492 |
| GII.4.1974 (SEQ ID NO:14) | G | S | H | D | T | N | L | K | A | Q | D | H | N | S | G | N | E | R | K |
| GII.4.1987 (SEQ ID NO:2) | V | S | H | D | T | N | L | K | A | Q | D | H | N | T | G | N | E | R | K |
| GII.4.1997 (SEQ ID NO:3) | A | S | H | D | T | N | M | K | E | Q | G | N | N | T | G | N | E | R | K |

B)

| Epitope | A | | | | | | B | | C | | D | | | E | | | F | | | |
|---|---|---|---|---|---|---|---|---|---|---|---|---|---|---|---|---|---|---|---|---|
| Amino Acids | 294 | 296 | 297 | 298 | 368 | 372 | 333 | 382 | 340 | 376 | 393 | 394 | 395 | 407 | 412 | 413 | 310 | 316 | 484 | 493 |
| GII.4.2002 (SEQ ID NO:4) | A | T | H | N | N | N | M | K | G | E | N | G | A | S | T | G | N | E | R | K |
| GII.4.2002a (SEQ ID NO:5) | A | T | H | N | N | N | M | K | G | E | N | G | T | S | T | G | N | E | R | K |
| GII.4.2004 (SEQ ID NO:6) | A | A | Q | N | S | S | V | R | R | E | S | T | T | D | D | S | N | E | R | K |
| GII.4.2005 (SEQ ID NO:7) | P | T | R | T | A | D | M | R | G | E | S | S | A | D | T | V | N | E | R | K |
| GII.4.2006 (SEQ ID NO:8) | A | S | R | N | S | E | V | K | G | E | S | T | T | S | N | V | N | E | R | K |
| GII.4.2007 (SEQ ID NO:9) | A | T | Q | E | S | S | V | R | R | E | S | T | T | N | D | S | N | E | R | K |
| GII.4.2008a (SEQ ID NO:10) | A | S | R | N | A | D | M | K | S | E | S | T | T | N | T | G | N | E | R | K |
| GII.4.2008s (SEQ ID NO:11) | S | S | R | N | A | D | V | K | A | D | N | T | A | S | N | S | S | E | R | K |
| GII.4.2009 (SEQ ID NO:12) | P | S | R | N | A | D | V | K | T | E | S | T | T | S | N | I | S | E | R | K |
| GII.4.2012 (SEQ ID NO:13) | T | S | R | N | E | D | V | K | T | E | G | T | T | S | N | T | D | E | R | K |

*FIG. 1*

| | 280 | 285 | 294 | 296 | 297 | 298 | 306 | 309 | 333 | 339 | 340 | 346 | 352 | 356 | 357 | 368 | 372 | 376 | 378 | 393 | 394 | 395 | 397 | 407 | 412 | 413 |
|---|---|---|---|---|---|---|---|---|---|---|---|---|---|---|---|---|---|---|---|---|---|---|---|---|---|---|
| GII.4-1987 | A | N | V | S | H | D | Q | S | L | R | A | A | S | V | H | T | N | Q | G | D | -- | H | Q | N | T | G |
| GII.4-2006 | P | T | A | S | R | N | L | N | V | K | G | G | Y | A | P | S | E | E | H | S | T | T | R | S | N | V |
The 5 predicted important antigenic epitopes in GII.4 noroviruses
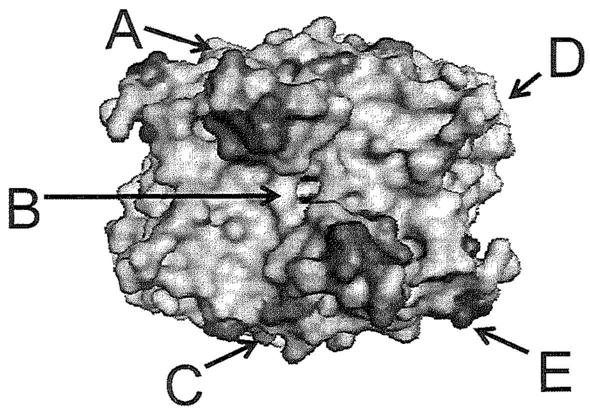
Chimeric VRPs used to immunize mice:
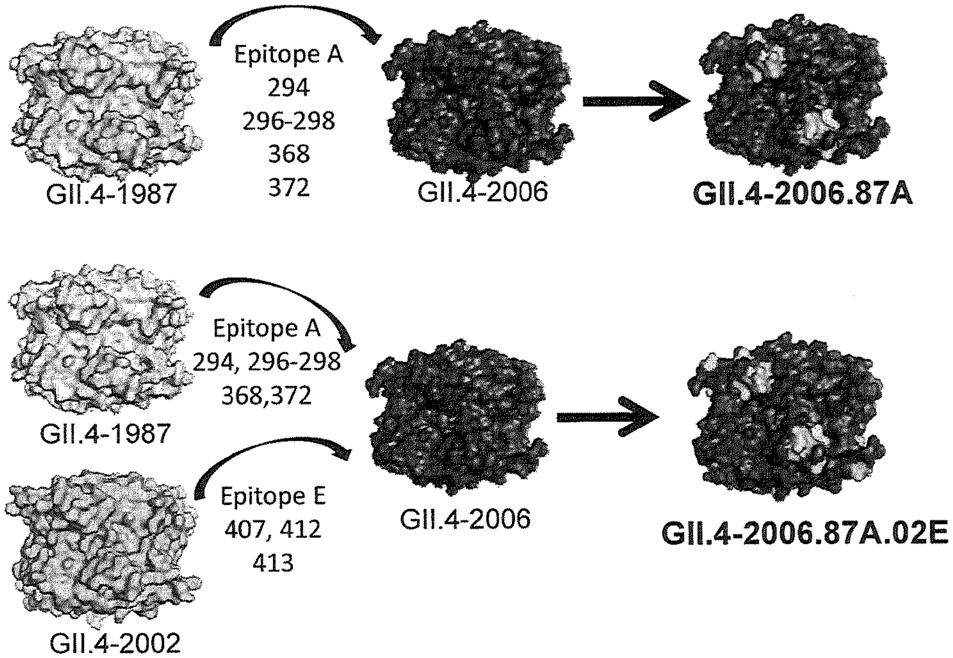
Figure 2

Mice were immunized with VRPs and boosted with the same VRPs on day 21. Seven days post-boost, mice were euthanized and serum was collected to use in ELISA-based assays to determine serum blockade response and reactivity to various VLPs.

Anti-1987 sera cannot block 2006 or 2009

- 1987
- 1997
- 2002
- 2006
- 2009
- 2006.87A
- 2006.87A.02E

Anti-2002 sera cannot block 2006 or 2009

- 1987
- 1997
- 2002
- 2006
- 2009
- 2006.87A
- 2006.87A.02E

Structural Model of Predicted Conserved GII.4 Norovirus Blockade Epitope

Identification of GII.4 Norovirus Conserved Blockade Epitope Using Human Monoclonal Antibodies.

SEQUENCE LISTING

```
<160> NUMBER OF SEQ ID NOS: 14

<210> SEQ ID NO 1
<211> LENGTH: 540
<212> TYPE: PRT
<213> ORGANISM: Norovirus Hu/GII.4/CHDC5191/1974/US

<400> SEQUENCE: 1

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Ser Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285
```

```
Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Met Leu Thr Gln
                325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 2
<211> LENGTH: 539
<212> TYPE: PRT
<213> ORGANISM: Human calicivirus Hu/NLV/GII/MD145-12/1987/US

<400> SEQUENCE: 2

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ser Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
```

-continued

```
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser His Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Asp Val Thr His Ile Val Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Ala Asp Gly Ser Thr Arg Ala His Lys Ala Thr Val Ser
            340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Ile
                485                 490                 495

Thr Val Ala His Thr Gly Pro Tyr Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Thr Gly Arg Arg Arg Ala Leu
    530                 535
```

<210> SEQ ID NO 3
<211> LENGTH: 539
<212> TYPE: PRT
<213> ORGANISM: Norovirus Hu/GII.4/1997/USA

<400> SEQUENCE: 3

```
Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Ile Thr His Ile Ala Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
```

-continued

```
    370                 375                 380

Pro Val Gly Val Ile Gln Asp Gly Gly Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535


<210> SEQ ID NO 4
<211> LENGTH: 540
<212> TYPE: PRT
<213> ORGANISM: Norovirus Hu/GII.4.2002/Farmington Hills

<400> SEQUENCE: 4

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205
```

```
Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Met Leu Thr Gln
                325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Ala His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

<210> SEQ ID NO 5
<211> LENGTH: 540
<212> TYPE: PRT
<213> ORGANISM: Norovirus GII.4.2002a

<400> SEQUENCE: 5

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45
```

-continued

```
Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Ser Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Met Leu Thr Gln
                325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460
```

-continued

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 6
<211> LENGTH: 540
<212> TYPE: PRT
<213> ORGANISM: Norovirus Hu/GII.4/Hunter 284E/04O/AU

<400> SEQUENCE: 6

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Val Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Leu Tyr His Tyr Asn Gln Ser Asn Asp Pro Thr Ile
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Met Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ala Gln Asn Tyr Thr Met Asn Leu Ala
    290                 295                 300
```

```
Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ser Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Ile Asn Gln Phe Tyr Thr Leu Ala
        515                 520                 525

Pro Met Gly Asn Gly Ala Gly Arg Arg Arg Ala Leu
    530                 535                 540


<210> SEQ ID NO 7
<211> LENGTH: 540
<212> TYPE: PRT
<213> ORGANISM: Norovirus Hu/Sakai/04-179/2005/JP

<400> SEQUENCE: 7

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
```

```
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Pro Gly Thr Arg Thr Tyr Arg Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Gly Asp Gly Ser Thr Arg Gly His Lys Ala Thr Val Ser
            340                 345                 350

Thr Gly Ser Val Asp Phe Thr Pro Lys Leu Gly Ser Val Gln Phe Ala
        355                 360                 365

Thr Asp Thr Asp Asn Asp Phe Glu Thr Gly Gln Asn Thr Arg Phe Thr
    370                 375                 380

Pro Val Gly Val Ile Gln Asp Gly Ser Ser Ala His Arg Asn Glu Pro
385                 390                 395                 400

Gln Gln Trp Val Leu Pro Asp Tyr Ser Gly Arg Thr Val His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ser Gln Ser Asp Val Ala Leu Leu Arg Phe Val Asn Pro
465                 470                 475                 480

Asp Thr Gly Arg Val Leu Phe Glu Cys Lys Leu His Lys Ala Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
    530                 535                 540

<210> SEQ ID NO 8
```

<211> LENGTH: 540
<212> TYPE: PRT
<213> ORGANISM: Norovirus Hu/GII.4/Minerva/2006/USA

<400> SEQUENCE: 8

```
Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Asp Gly Ser Thr Arg Gly His Lys Ala Thr Val Tyr
            340                 345                 350

Thr Gly Ser Ala Pro Phe Thr Pro Lys Leu Gly Ser Val Gln Phe Ser
        355                 360                 365

Thr Asp Thr Glu Asn Asp Phe Glu Thr His Gln Asn Thr Lys Phe Thr
    370                 375                 380

Pro Val Gly Val Ile Gln Asp Gly Ser Thr Thr His Arg Asn Glu Pro
```

385 390 395 400

Gln Gln Trp Val Leu Pro Ser Tyr Ser Gly Arg Asn Val His Asn Val
405 410 415

His Leu Ala Pro Ala Val Ala Pro Thr Phe Pro Gly Glu Gln Leu Leu
420 425 430

Phe Phe Arg Ser Thr Met Pro Gly Cys Ser Gly Tyr Pro Asn Met Asp
435 440 445

Leu Asp Cys Leu Leu Pro Gln Glu Trp Val Gln His Phe Tyr Gln Glu
450 455 460

Ala Ala Pro Ala Gln Ser Asp Val Ala Leu Leu Arg Phe Val Asn Pro
465 470 475 480

Asp Thr Gly Arg Val Leu Phe Glu Cys Lys Leu His Lys Ser Gly Tyr
485 490 495

Val Thr Val Ala His Thr Gly Gln His Asp Leu Val Ile Pro Pro Asn
500 505 510

Gly Tyr Phe Arg Phe Asp Ser Trp Val Asn Gln Phe Tyr Thr Leu Ala
515 520 525

Pro Met Gly Asn Gly Thr Gly Gly Arg Arg Ala Leu
530 535 540

<210> SEQ ID NO 9
<211> LENGTH: 540
<212> TYPE: PRT
<213> ORGANISM: Norovirus Hu/GII.4/cruiseship/2007/ZAF

<400> SEQUENCE: 9

Met Lys Met Ala Ser Ser Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Ser Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Thr Glu Gly Leu Ser Pro Ser Gln Val Thr Met Phe Pro His Ile
130 135 140

Ile Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

-continued

```
Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Arg Ile Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asn Tyr Ser Gly Arg Asp Ser His Asn Val
                405                 410                 415

His Leu Ala Pro Ala Val Ala Pro Ser Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

<210> SEQ ID NO 10
<211> LENGTH: 540
<212> TYPE: PRT
<213> ORGANISM: Norovirus Hu/GII.4/Armidale/NSW390I/2008/AU

<400> SEQUENCE: 10

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60
```

-continued

```
Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Arg Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Ser Asp Gly Ser Thr Arg Gly His Lys Ala Thr Val Leu
            340                 345                 350

Thr Gly Ser Ala Asp Phe Ala Pro Lys Leu Gly Arg Val Gln Phe Ala
        355                 360                 365

Thr Asp Thr Asp Asn Asp Phe Glu Ser Gly Gln Asn Thr Lys Phe Thr
    370                 375                 380

Pro Val Gly Val Ile Gln Asp Gly Ser Thr Thr His Arg Asn Glu Pro
385                 390                 395                 400

Gln Gln Trp Val Leu Pro Asn Tyr Ser Gly Arg Thr Gly His Asn Val
                405                 410                 415

His Leu Ala Pro Ala Val Ala Pro Thr Tyr Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480
```

```
Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 11
<211> LENGTH: 540
<212> TYPE: PRT
<213> ORGANISM: Norovirus Hu/GII.4/Stockholm/19865/2008/SE

<400> SEQUENCE: 11

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ser Gly Ser Arg Asn Tyr Thr Met Asn Leu Ala
    290                 295                 300

Thr Gln Asn Trp Asn Ser Tyr Asp Pro Thr Glu Glu Ile Pro Ala Pro
305                 310                 315                 320
```

-continued

```
Leu Gly Thr Pro Asp Phe Val Gly Lys Ile Gln Gly Val Leu Thr Gln
                325                 330                 335

Thr Thr Arg Ala Asp Gly Ser Thr Arg Gly His Lys Ala Thr Val Tyr
            340                 345                 350

Thr Gly Ser Ala Asp Phe Ala Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 12
<211> LENGTH: 540
<212> TYPE: PRT
<213> ORGANISM: Norovirus Hu/GII.4/New Orleans1805/2009/USA

<400> SEQUENCE: 12

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
```

```
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Pro Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asn Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Asp Asn Asp Phe Glu Thr Asn Gln Asn Thr Lys Phe Thr
    370                 375                 380

Pro Val Gly Val Ile Gln Asp Gly Ser Thr Thr Pro Arg Asn Glu Pro
385                 390                 395                 400

Gln Gln Trp Val Leu Pro Ser Tyr Ser Gly Arg Asn Ile His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

<210> SEQ ID NO 13
<211> LENGTH: 540
<212> TYPE: PRT
<213> ORGANISM: Norovirus Hu/GII.4/Sydney/NSW0514/2012/AU

<400> SEQUENCE: 13

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
```

```
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 14
<211> LENGTH: 539
<212> TYPE: PRT
<213> ORGANISM: Norovirus Hu/GII.4/CHDC5191/1974/US

<400> SEQUENCE: 14

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ser Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ala His Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240
```

-continued

```
Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Asp Val Thr Arg Val Gly Ile Ser His Asp Tyr Thr Met Asn Leu Val
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Ala Asp Gly Ser Thr Arg Ala His Lys Ala Thr Val Ser
            340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Thr Ser Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Ile
                485                 490                 495

Thr Val Ala His Thr Gly Pro Tyr Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Thr Gly Arg Arg Arg Ala Leu
    530                 535
```

METHODS AND COMPOSITIONS FOR NOROVIRUS BLOCKADE EPITOPES

STATEMENT OF PRIORITY

This application claims the benefit of U.S. Provisional Application Ser. No. 61/798,946, filed Mar. 15, 2013, the disclosure of which is incorporated by reference herein in its entirety.

STATEMENT REGARDING ELECTRONIC FILING OF A SEQUENCE LISTING

A Sequence Listing, in ASCII text format, submitted under 37 C.F.R. § 1.821, entitled 5470-659TSv2_ST25.txt, 66,007 bytes in size, generated on Jun. 28, 2016 and filed via EFS-Web, is provided in lieu of a paper copy. This Sequence Listing is hereby incorporated by reference into the specification for its disclosures.

STATEMENT OF GOVERNMENT SUPPORT

This invention was made with government support under Grant No. AI 056351 awarded by the National Institutes of Health. The United States government has certain rights in the invention.

FIELD OF THE INVENTION

The present invention relates to compositions comprising norovirus blockade epitopes and methods of their use in therapeutic and diagnostic applications.

BACKGROUND OF THE INVENTION

Noroviruses are the leading cause of severe viral gastroenteritis and are responsible for 50% of all acute gastroenteritis outbreaks in the United States and Europe [1]. Although the severity of disease is usually moderate, lasting 1-3 days, infection can be especially virulent in young children, the elderly, and the immunocompromised, with the latter group experiencing chronic diarrhea and virus shedding for over a year [2-8]. Importantly, it is estimated that 200,000 people die each year from norovirus infections, primarily children in the developing world [9]. An effective vaccine would be particularly advantageous for the very young and aged populations, military personnel, children and healthcare providers, food handlers, cruise ship passengers, and populations of the developing world [10]. Immunotherapeutics are especially needed for treating immunosuppressed populations experiencing long-term infections with chronic diarrhea. The lack of understanding of the extensive antigenic relationships among the large number of norovirus strains and the complex relationship between host protective immunity and virus antigenic heterogeneity are the primary obstacles to norovirus vaccine development.

The present invention overcomes previous shortcoming in the art by providing norovirus blockade epitopes and methods of their use in therapeutic and diagnostic applications.

SUMMARY OF THE INVENTION

The present invention provides a chimeric norovirus capsid protein comprising a norovirus VP1 major capsid protein backbone comprising a norovirus epitope selected from the group consisting of: a) Epitope A; b) Epitope B; c) Epitope C; d) Epitope D; e) Epitope E; f) Epitope F; and g) any combination of (a) through (f) above, wherein the norovirus epitope is from a norovirus strain that is different from the norovirus VP1 major capsid protein backbone.

Also provided herein is a synthetic backbone molecule comprising a norovirus epitope selected from the group consisting of: a) Epitope A; b) Epitope B; c) Epitope C; d) Epitope D; e) Epitope E; f) Epitope F; and g) any combination of (a) through (f) above, wherein the backbone molecule allows for formation of a conformational epitope.

Further provided herein is a norovirus P particle comprising a norovirus epitope selected from the group consisting of: a) Epitope A; b) Epitope B; c) Epitope C; d) Epitope D; e) Epitope E; f) Epitope F; and g) any combination of (a) through (f) above, wherein the epitope(s) are presented on the P particle surface.

In addition, the present invention provides a mimitope comprising a norovirus epitope selected from the group consisting of: a) Epitope A; b) Epitope B; c) Epitope C; d) Epitope D; e) Epitope E; f) Epitope F; and g) any combination of (a) through (f) above.

The present invention further provides therapeutic methods. Thus, in one embodiment, the present invention provides a method of producing an immune response to a norovirus in a subject, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

Also provided herein is a method of treating a norovirus infection in a subject in need thereof, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

Further provided herein is a method of preventing a norovirus infection in a subject, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

In additional embodiments, the present invention provides a method of protecting a subject from the effects of norovirus infection, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

The present invention also provides diagnostic methods. Thus, in one aspect, the present invention provides a method of detecting a neutralizing antibody to a norovirus, the method comprising determining whether an antibody binds to the chimeric norovirus capsid protein of this invention, the synthetic backbone molecule of this invention, the P particle of this invention, the mimitope of this invention, the VRP of this invention and/or the VLP of this invention, wherein binding by the antibody to the chimeric norovirus capsid protein of this invention, the synthetic backbone molecule of this invention, the P particle of this invention, the mimitope of this invention, the VRP of this invention and/or the VLP of this invention indicates that the antibody is a neutralizing antibody to a norovirus.

A method is also provided herein of identifying a neutralizing antibody to a norovirus, comprising: (a) contacting an antibody with the chimeric norovirus capsid protein of this invention, the synthetic backbone molecule of this invention, the P particle of this invention, the mimitope of this invention, the VRP of this invention and/or the VLP of this invention; and (b) determining if the antibody binds to the chimeric norovirus capsid protein of this invention, the synthetic backbone molecule of this invention, the P particle of this invention, the mimitope of this invention, the VRP of this invention and/or the VLP of this invention, wherein binding by the antibody to the chimeric norovirus capsid protein of this invention, the synthetic backbone molecule of this invention, the P particle of this invention, the mimitope of this invention, the VRP of this invention and/or the VLP of this invention identifies the antibody as a neutralizing antibody to a norovirus.

In further embodiments, the present invention provides a method of identifying an immunogenic composition that induces a neutralizing antibody to a norovirus in a subject, the method comprising: (a) contacting a biological sample from a subject that has been administered the immunogenic composition with the chimeric norovirus capsid protein of this invention, the synthetic backbone molecule of this invention, the P particle of this invention, the mimitope of this invention, the VRP of this invention and/or the VLP of this invention; (b) determining if the biological sample comprises an antibody that binds the chimeric norovirus capsid protein of this invention, the synthetic backbone molecule of this invention, the P particle of this invention, the mimitope of this invention, the VRP of this invention and/or the VLP of this invention; and (c) identifying the immunogenic composition as inducing a neutralizing antibody to a norovirus in the subject if the biological sample comprises an antibody that binds to the chimeric norovirus capsid protein of this invention, the synthetic backbone molecule of this invention, the P particle of this invention, the mimitope of this invention, the VRP of this invention and/or the VLP of this invention.

Also provided herein is a method of identifying an immunogenic composition that induces a neutralizing antibody to a norovirus in a subject, the method comprising: (a) administering an immunogenic composition comprising a norovirus antigen to a subject in an amount effective to induce antibodies against the norovirus antigen; (b) contacting a biological sample from the subject with the chimeric norovirus capsid protein of this invention, the synthetic backbone molecule of this invention, the P particle of this invention, the mimitope of this invention, the VRP of this invention and/or the VLP of this invention; (c) determining if the biological sample comprises an antibody that binds the chimeric norovirus capsid protein of this invention, the synthetic backbone molecule of this invention, the P particle of this invention, the mimitope of this invention, the VRP of this invention and/or the VLP of this invention; and (d) identifying the immunogenic composition as inducing a neutralizing antibody to a norovirus in the subject if the biological sample comprises an antibody that binds the chimeric norovirus capsid protein of this invention, the synthetic backbone molecule of this invention, the P particle of this invention, the mimitope of this invention, the VRP of this invention and/or the VLP of this invention.

BRIEF DESCRIPTION OF THE DRAWINGS

FIG. 1, Panels A and B depict the evolutionary profile of epitopes of various human norovirus (NoV) strains. The evolution of the GII.4 noroviruses was assessed over a 36 year period of time by comparing strains from 1974 to 2010. In comparing these sequences, sites of variation in the p2 subdomain were noted, and these sites were mapped onto the crystal structure of the P-domain dimer for the 1997 strain VA387. Surface-exposed sites of variation were then examined to determine which residues were close enough to constitute a single epitope, and epitopes A-F were predicted based upon this variation. VLPs containing substituted Epitopes A through F were created and tested for ability to bind to surrogate neutralizing antibodies in the VLP-HBGA blockade assay. Epitopes A, D, E and F were confirmed to be blockade epitopes. Numbering of amino acids is based on amino acid position of the full amino acid sequence of the norovirus strains listed as provided in the GENBANK® Database or as provided herein. For example, the numbering of amino acids can be based on the amino acid sequence of GII.4.2002 (OENBANK® Database Accession No. AFJ04708.1 for amino acid sequence; GENBANK® Database Accession No. JQ478408 for nucleotide sequence), provided herein as SEQ ID NO:4). For GII.4.1974 (SEQ ID NO:14), GII.4.1987 (SEQID NO:2) and GII.4.1997 (SEQ ID NO:3), the amino acids of Epitope D are 393 and 394; the amino acids of Epitope E are 406, 411 and 412; and the amino acids of Epitope F are 310, 216, 483 and 492, as shown in Panel A. The amino acids for Epitope D of the other listed norovirus strains are 393, 394 and 395; the amino acids of Epitope E of the other listed norovirus strains are 407, 412, and 413; and the amino acids of Epitope F of the other listed norovirus strains are 310, 316, 484 and 493, as shown in Panel B, based on an insertion of an amino acid at position 394 in these subsequently listed strains. Norovirus strain GII.4.1974: SEQ ID NO:4, norovirus strain GII.4.1987: SEQ ID NO:2, norovirus strain GII.4.1997: SEQ ID NO:3, norovirus strain GII.4.2002: SEQ ID NO:4, norovirus strain GII.4.2002a: SEQ ID NO:5, norovirus strain GII.4.2004: SEQ ID NO:6, norovirus strain GII.4.2005: SEQ ID NO:7, norovirus strain GII.4.2006: SEQ ID NO:8, norovirus strain GII.4.2007: SEQ ID NO:9, norovirus strain GII.4.2008a: SEQ ID NO:10, norovirus strain GII.4.2008s: SEQ ID NO:11, norovirus strain GII.4.2009: SEQ ID NO:12, or norovirus strain GII.4.2012: SEQ ID NO:13.

FIG. 2 depicts chimeric VRPs used to immunize mice. Norovirus strain GII.4.1987: SEQ ID NO:2, norovirus strain GII.4.2006: SEQ ID NO:8.

DETAILED DESCRIPTION OF THE INVENTION

Figure 3:
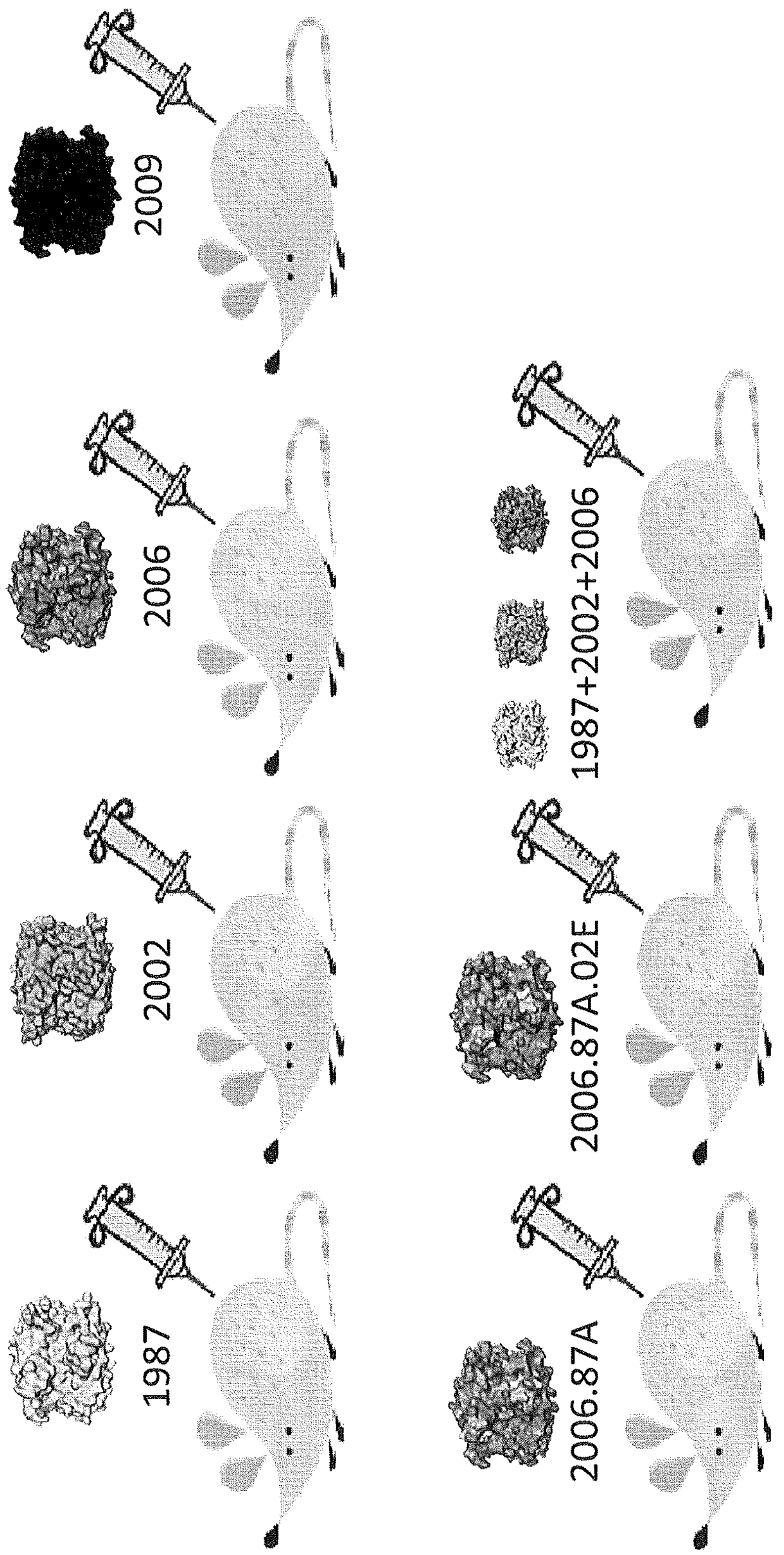
FIG. 3 depicts the immunization of mice with GII.4 parental or chimeric capsids.

Noroviruses are single-stranded, positive sense RNA viruses that belong to the family *Caliciviridae*. The norovirus genome is ~7.5 kb and contains three open reading frames. ORF1 encodes the non-structural proteins, ORF2 encodes the VP1 major capsid protein, and ORF3 encodes the VP2 minor capsid protein. VP1 is divided into three parts: the shell, which forms the inner-most portion of the virion; the P1 subdomain, which forms a stalk-like projection away from the virion surface; and the P2 subdomain, which is a highly variable, surface exposed region that sits on top of P1. The P2 subdomain of the VP1 major capsid protein contains potential neutralizing antibody epitopes. These epitopes change over time, likely allowing new strains to escape human herd immunity.

An effective GII.4 norovirus vaccine needs to address these antigenic changes over time. The present invention is based on the identification and characterization of various neutralizing blockade epitopes in norovirus capsid protein. Thus, in one aspect, the present invention provides a chimeric norovirus capsid protein comprising a norovirus VP1 major capsid protein backbone comprising a norovirus epitope selected from the group consisting of: a) Epitope A; b) Epitope B; c) Epitope C; d) Epitope D; e) Epitope E; f) Epitope F; and g) any combination of (a) through (f) above, wherein the norovirus epitope is from a norovirus strain that is different from the norovirus ORF2 major capsid protein backbone.

Also provided herein is a synthetic backbone molecule comprising a norovirus epitope selected from the group consisting of: a) Epitope A; b) Epitope B; c) Epitope C; d) Epitope D; e) Epitope E; f) Epitope F; and g) any combination of (a) through (f) above, wherein the backbone molecule allows for formation of the conformational epitope.

Further provided herein is a norovirus P particle comprising a norovirus epitope selected from the group consisting of: a) Epitope A; b) Epitope B; c) Epitope C; d) Epitope D; e) Epitope E; f) Epitope F; and g) any combination of (a) through (f) above, wherein the epitope(s) are presented on the P particle surface.

In addition, the present invention provides a mimitope comprising a norovirus epitope selected from the group consisting of: a) Epitope A; b) Epitope B; c) Epitope C; d) Epitope D; e) Epitope E; f) Epitope F; and g) any combination of (a) through (f) above.

In some embodiments of the chimeric norovirus capsid protein of this invention, the norovirus VP1 major capsid protein backbone can be from any norovirus strain and in some embodiments can be from a genogroup GII, genotype 4 (GII.4) strain.

In some embodiments, of the chimeric norovirus capsid protein of this invention, the norovirus VP1 major capsid protein backbone can be from GII.4.1974 (GENBANK® Database Accession No. ACT76139.1; SEQ ID NO:14), GII.4.1987 (GENBANK® Database Accession No. AAK50355.1: SEQ ID NO:2), GII.4.1997 (GENBANK® Database Accession No. JQ478407; SEQ ID NO:3), GII.4.2002a (SEQ ID NO:5), GII.4.2002 (GENBANK® Database Accession No. JQ478408; SEQ ID NO:4), GII.4.2004 (GENBANK® Database Accession No. AAZ31376.2; SEQ ID NO:6), GII.4.2005 (GENBANK® Database Accession No. BAE98194.1; SEQ ID NO:7), GII.4.2006 (GENBANK® Database Accession No. JQ478409; SEQ ID NO:8), GII.4.2007 (GENBANK® Database Accession No. AB496912.1; SEQ ID NO:9), GII.4.2008s (GENBANK® Database Accession No. BAH30707.1; SEQ ID NO: 11), GII.4.2008a (GENBANK® Database Accession No. ACX31885.1; SEQ ID NO: 10), GII.4.2009 (GENBANK® Database Accession No. ADD10375; SEQ ID NO: 12), or GII.4.2012 (GENBANK® Database Accession No. JX459908; SEQ ID NO:13).

The amino acid sequence of GII.4.2002a is as follows (SEQ ID NO:5). mkmasndanpsdgstanlvpevnnevmalepv-vgaaiaapvagqqnvidpwirnnfvqapggeftvspmapgeilwsapl gpdlnpylshlarmyngyaggfevqvilagnaftagkiifaavppnfpteglsp-sqvtmfphiivdvrqlepvliplpdvrnnfyh ynqsndptikliamlytplran-nagedvftvscrvltrpspdfdfiflvpptvesrtksftypiltveemtnsrfpiple-klftgpsgafv vqpqngratdgvllgttqlspvnictfrgdvthiagthnytm-nlasqnwnnydpteeipaplgtpdfvgriqgmltqttrgdgstrg hkatvstgd-vhftpklgsiqfntdtnndfetgqntkftpvgvvqdgngthqnepqqwvlp-sysgrtghnvhlapavaptfpgeqll ffrstmpgcsgypnmnldcllpqe-wvqhfyqeaapaqsdvallrfvnpdtgrvlfecklhksgyvtvahtgqhdlv-ippngyfrf dswvnqfytlapmgngtgrrral In various embodiments, the chimeric norovirus capsid protein of this invention, the synthetic backbone molecule of this invention, the norovirus P particle of this invention and/or the mimitope of this invention can comprise Epitope A (amino acids 294, 296, 297, 298, 368 and 372) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012.

In various embodiments, the chimeric norovirus capsid protein of this invention, the synthetic backbone molecule of this invention, the norovirus P particle of this invention and/or the mimitope of this invention can comprise Epitope B (amino acids 333 and 382) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012.

In various embodiments, the chimeric norovirus capsid protein of this invention, the synthetic backbone molecule of this invention, the norovirus P particle of this invention and/or the mimitope of this invention can comprise Epitope C (amino acids 340 and 376) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012.

In various embodiments, the chimeric norovirus capsid protein of this invention, the synthetic backbone molecule of this invention, the norovirus P particle of this invention and/or the mimitope of this invention can comprise Epitope D (amino acids 393, 394 and 395) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012, wherein Epitope D is from a norovirus strain different from the norovirus ORF2 major capsid protein backbone.

In various embodiments, the chimeric norovirus capsid protein of this invention, the synthetic backbone molecule of this invention, the norovirus P particle of this invention and/or the mimitope of this invention can comprise Epitope E (amino acids 407, 412 and 413) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012, wherein Epitope E is from a norovirus strain different from the norovirus ORF2 major capsid protein backbone.

In various embodiments, the chimeric norovirus capsid protein of this invention, the synthetic backbone molecule of this invention, the norovirus P particle of this invention and/or the mimitope of this invention can comprise. Epitope F (amino acids 310, 316, 484 and 493) from GII.4.1974, GII.4.1987, GII.4.1997, GII.4.2002a, GII.4.2002, GII.4.2004, GII.4.2005, GII.4.2006, GII.4.2007, GII.4.2008s, GII.4.2008a, GII.4.2009 or GII.4.2012.

In some embodiments of the chimeric norovirus capsid protein of this invention, the norovirus ORF2 major capsid protein backbone can be from GII.4.2006 and can comprise Epitope A from GII.4.1987 and Epitope E from GII.4.2002.

The present invention further provides an isolated nucleic acid molecule encoding the chimeric norovirus capsid protein of this invention, a vector comprising the nucleic acid molecule of this invention and a cell comprising the capsid protein, nucleic acid molecule and/or vector of this invention.

In some embodiments, the present invention provides a Venezuelan Equine Encephalitis (VEE) replicon particle (VRP) comprising the nucleic acid molecule of this invention.

In some embodiments, the present invention provides a virus like particle (VLP) comprising the chimeric norovirus capsid protein of this invention.

The present invention also provides a composition comprising the chimeric norovirus capsid protein of this invention, the synthetic backbone molecule of this invention, the P particle of this invention, the mimitope of this invention, the nucleic acid molecule of this invention, the vector of this invention, the VRP of this invention and/or the VLP of this invention in a pharmaceutically acceptable carrier.

In some embodiments of the invention the individual and conformational epitopes of the norovirus capsid proteins can be presented on a synthetic backbone or support structure so that the epitopes within the synthetic backbone or support structure mimic the conformation and arrangement of the epitopes within the structure of the norovirus capsid protein, VLP or VRP.

In still further embodiments of the invention, the present invention provides peptide mimitopes (see, Meloen et al. (2000) *J. Mol. Recognit.* 13, 352-359) that mimic the individual and conformational epitopes of the norovirus capsid proteins of the invention. Mimitopes may be identified using any technique known in the art, such as by surface stimulation, random peptide libraries or phage display libraries, using an antibody or antibodies to the individual and conformational epitopes of the chimeric norovirus capsid proteins of the invention.

In yet further embodiments of this invention a norovirus P particle (see, Tan et al. (2011) *J. Virol.* 85(2), 753-764) is provided that presents the epitopes of the norovirus capsid proteins as described herein.

In an aspect of the chimeric VLP/VRP/virus vaccine approach of the invention, one or more of the identified potential neutralization epitopes from one or more donor strains is moved into any other GII.4 norovirus backbone strain to induce broad protection against multiple strains. In another aspect of the invention, moving epitope A from GII.4.1987 and epitope E from GII.4.2002 into the GII.4.2006 backbone induces a broadly blocking immune response in mice against GII.4 strains GII.4.1987, 2002, 2006, 2009, and 2012. Thus, by vaccine that incorporates epitope(s) from one or more circulating strains into the backbone of another strain can induce protection against multiple norovirus strains.

In a further aspect of the invention, in order to create a chimeric norovirus construct, the full-length ORF2 major capsid gene sequence from norovirus is either cloned from a patient sample or produced as a synthetic construct (e.g., from a commercial source). Natural or engineered endonuclease sites are used to insert sequence containing the desired epitope changes for one or more GII.4 strains. Alternatively, in yet another aspect of the invention, the full-length capsid may be synthesized (e.g., using a consensus sequence) with the desired sequence changes already present. After production of the desired full-length chimeric GII.4 norovirus capsid gene, this gene is then cloned into an expression vector. Upon expression, the VP1 major capsid protein self-assembles into VLPs, which can then be purified. Alternatively, VRPs expressing the major capsid protein can be produced and purified and subsequently used as a vaccine or used as a source of VLP production.

The term "chimeric norovirus capsid protein" and similar terms will be understood in the art to mean a norovirus capsid protein derived from a particular norovirus strain that contains single or multiple amino acid substitutions at various positions in which the amino acid substitution(s) is an amino acid(s) that is one from the corresponding position(s) of a norovirus capsid protein from a different norovirus strain. In representative embodiments, the amino acid substitution comprises a particular epitope from a norovirus strain different from that of the capsid protein in which the substitution is made. In further embodiments, the amino acid substitution(s) may be at amino acids 294, 296-298, 368 and 372 (Epitope A) of the norovirus VP1 major capsid protein encoded by ORF2 of human norovirus (hNoV). In other embodiments, the substitution(s) may be at amino acids 333 and 382 (Epitope B) of the hNoV VP1 major capsid protein. In other embodiments, the substitution(s) may be at amino acids 340 and 376 (Epitope C) of the hNoV VP1 major capsid protein. In other embodiments, the substitution(s) may be at amino acids 393-395 (Epitope D) of the hNoV VP1 major capsid protein. In other embodiments, the substitution(s) may be at amino acids 407, 412 and 413, or amino acids 406, 411 and 412, (Epitope E) of the hNoV VP1 major capsid protein. In still further embodiments, the amino acid substitution(s) may be at amino acid positions 304-306, 309 and 310 (Epitope F) of the hNoV VP1 major capsid protein. In still further embodiments, the amino acid substitutions may comprise any two or more of these epitopes, in any combination. In a particular embodiment, the combination of amino acid substitutions may be from Epitopes A and F.

The term "norovirus capsid protein backbone" and similar terms refer to the particular norovirus capsid protein from which a chimeric norovirus capsid protein is based. The norovirus capsid protein backbone may be from any genogroup, genotype and strain of hNoV. In an embodiment of the invention, the norovirus capsid protein backbone is from genogroup II and genotype 4 (GII.4) of hNoV. In an embodiment, the norovirus capsid protein backbone may be from GII.4-1974 (GENBANK® Database Accession No. ACT76139.1; SEQ ID NO: 14). In another embodiment, the norovirus capsid protein backbone may be from GII.4-1987 (GENBANK® Database Accession No. AAK50355.1; SEQ ID NO:2). In another embodiment, the norovirus capsid protein backbone may be from GII.4-1997 (GENBANK® Database Accession No. AFJ04707.1 SEQ ID NO:3). In another embodiment, the norovirus capsid protein backbone may be from GII.4-2002 (GENBANK® Database Accession No. AFJ4708.1; SEQ ID NO:4). In another embodiment, the norovirus capsid protein backbone may be from GII.4-2004 (GENBANK® Database Accession No. AAZ31376.2; SEQ ID NO:6). In another embodiment, the norovirus capsid protein backbone may be from 011.4-2005 (GENBANK® Database Accession No. BAE98194.1; SEQ ID NO:7). In another embodiment, the norovirus capsid protein backbone may be from GII.4-2006 (GENBANK® Database Accession No. AFJ4709.1; SEQ ID NO:8). In another embodiment, the norovirus capsid protein backbone may be from GII.4-2007 (GENBANK® Database Accession No. BAH56690.1; SEQ ID NO:9). In another embodiment, the norovirus capsid protein backbone may be from GII.4-2008a (GENBANK® Database Accession No. ACX31885.1; SEQ ID NO: 10). In another embodiment, the norovirus capsid protein backbone may be from GII.4-2008s (GENBANK® Database Accession No. BAH30307.1; SEQ ID NO:11). In another embodiment, the norovirus capsid protein backbone may be from GII.4-2009 (GENBANK® Database Accession No. ADD10375.1; SEQ ID NO: 12). In another embodiment, the norovirus capsid protein backbone may be from GII.4-2012 (GENBANK® Database Accession No. AFV08795.1; SEQ ID NO:13).

The epitope of the chimeric norovirus capsid protein may be from any norovirus genogroup, genotype and strain, as long as it different from that of the norovirus capsid protein backbone. In a particular embodiment, wherein the norovirus capsid protein backbone is from GII.4-2006, the epitope is epitope A from GII.4-1987. In another particular embodiment, wherein, the norovirus capsid protein backbone is from GII.4-2006, the epitopes can be a combination of Epitope A from GII.1987 and Epitope E from GII.4-2002.

The invention further provides a nucleic acid (e.g., isolated nucleic acid) encoding a chimeric norovirus capsid protein or a polypeptide of the invention.

The invention further provides a nucleic acid molecule (e.g., an isolated nucleic acid molecule) encoding a chimeric norovirus VLP, a chimeric norovirus VRP or a viral coat of a chimeric norovirus particle of the invention.

Also provided are vectors encoding the nucleic acid molecules of the invention.

Also provided are cells that comprise the vectors, nucleic acid molecules, norovirus epitopes, polypeptides, chimeric norovirus VLPs, chimeric norovirus VRPs or chimeric norovirus particles of the invention.

The invention also provides immunogenic compositions comprising the cells, vectors, nucleic acid molecules, norovirus epitopes, chimeric norovirus capsid proteins, polypeptides, chimeric norovirus VLPs, chimeric norovirus VRPs, or chimeric norovirus particles of the invention in a pharmaceutically acceptable carrier. In embodiments, the immunogenic composition is monovalent. In embodiments, the immunogenic composition is multivalent for different norovirus serotypes.

The invention encompasses methods of producing an immune response to a norovirus in a subject, the method comprising administering to the subject an effective amount of a norovirus epitope, a chimeric norovirus capsid protein, a polypeptide, a chimeric norovirus VLP, a chimeric norovirus VRP or chimeric norovirus particle, nucleic acid molecule, vector, cell or immunogenic composition of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of norovirus infection.

"Effective amount" as used herein refers to an amount of a vector, nucleic acid molecule, epitope, polypeptide, cell, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The terms "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing norovirus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating norovirus infection in a subject, whether against one or multiple strains, genotypes or genogroups of norovirus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to norovirus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by norovirus. Alternatively, a subject according to the invention can also include a subject not previously known or suspected to be infected by norovirus or in need of treatment for norovirus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

A "subject in need" of the methods of the invention can be a subject known to be, or suspected of being, infected with, or at risk of being infected with, norovirus.

Pharmaceutical formulations (e.g., immunogenic formulation) comprising the norovirus epitopes, chimeric norovirus capsid proteins, polypeptides, chimeric norovirus VLPs, chimeric norovirus VRPs or chimeric norovirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science and Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., *Vaccine* 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science and Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally nontoxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 μg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

In embodiments of the invention, the dosage of a virus particle of this invention can be in a range of about $10^3$ to about $10^8$ plaque forming units (PFUs). In embodiments of this invention, the dosage of a VLP of this invention can be in a range of about 5 micrograms to 5 milligrams. In embodiments of this invention, the dosage of a protein of this invention can be in a range of about 10 to about $10^5$ micrograms +/− adjuvant.

EXAMPLES

Noroviruses are ~38 nm icosahedral viruses with a ~7.5 Kb single-stranded, positive-sense RNA genome that encodes three large open reading frames (ORFs). ORF1 encodes the non-structural proteins, ORFs 2 and 3 encode the major and minor capsid proteins, respectively. Expression of the major capsid protein (ORF2) in Venezuelan equine encephalitis (VEE) virus or baculovirus results in the formation of virus-like particles (VLPs) composed of 90 copies of the major capsid protein dimer [11]. Noroviruses are grouped by the amino acid sequence of the major capsid protein. Viruses with less than 14.3% difference are classified as the same strain, 14.3-43.8% the same genotype, and 45-61.4% the same genogroup [12]. Currently, noroviruses are grouped into five genogroups (GI-GV). Genogroups GI and GII are responsible for most human infections and are further subdivided into 8 and 21 different genotypes, respectively [1, 12].

Structurally, the capsid monomer is divided into three domains. The shell domain (S) forms the core of the particle and the protruding domain (P) extends away from the core. The P domain is further subdivided into the P1 subdomain (residues 226-278 and 406-520) and the P2 subdomain (residues 279-405) [11]. The P2 subdomain is the most exposed region of the viral particle and it is well positioned to interact with potential neutralizing antibodies and histo-blood group antigen (HBGA) ligands [13-17]. Previous studies have shown that the P2 subdomain of the major capsid protein of GII.4 strains is evolving rapidly, resulting in new epidemic strains with altered carbohydrate ligand binding properties and antigenicity [13, 18-23].

For the past two decades, the majority of norovirus outbreaks have been caused by strains within the genogroup II, genotype 4 (GII.4 strains) subcluster. Between 1995 and 2006, four major norovirus pandemics associated with GII.4 strains were characterized using molecular epidemiologic methods. During the mid-1990s [24] strain US95/96 was responsible for ~55% of the norovirus outbreaks in the USA and 85% of the outbreaks in the Netherlands [25]. In 2002, the US95/96 strain was replaced by the Farmington Hills strain [26], which was associated with ~80% of norovirus outbreaks [27] in the USA. In 2004, the Hunter GII.4 variant was detected in Australia, Europe, and Asia [28-30]. Hunter strains were largely replaced in 2006 by two new co-circulating GII.4 variants in the USA and Europe; Laurens (2006a) and Minerva (2006b) [5, 29, 31]. In 2009 GII.4.2009 New Orleans [1, 32] emerged and replaced Minerva, followed in 2012 by pandemic circulation of GII.4.2012 Sydney [33].

A variety of studies using time ordered human outbreak sera and mouse monoclonal antibodies support the hypothesis that the GII.4 noroviruses are undergoing antigenic variation and that this variation contributes to the emergence of new outbreak strains over time [13, 22, 34-36]. However, the lack of a cell culture or small animal model for human norovirus cultivation restricts study of neutralization antibodies and epitopes. To circumvent this problem, highly informative in vitro assays have been developed that measure the ability of an antibody to "block" binding of a VLP to a carbohydrate ligand [13, 17, 37, 38]. This assay is highly sensitive, as it differentiates between norovirus strains too similar to be distinguished by ETA. The clinical relevance of the blockade assay, as a surrogate neutralization assay, has been confirmed in both infected chimpanzees [39] and Norwalk virus-infected humans [10, 40]. Using human norovirus outbreak sera, VLP-immunized mouse sera and mouse mAbs [13, 35, 36], the early 011.4 strains (1987 and 1997) were antigenically indistinguishable from each other by EIA and surrogate neutralization assays. VLPs of strains circulating post 2002 had significantly less reactivity with sera directed against earlier strains and no reactivity to mouse mAbs directed to 011.4.1987. Conversely, select mouse mAbs generated against GII.4.2006 reacted with VLPs that circulated only from 2002 or later. No blockade antibodies were found to be in common between GII.4.1987 and GII.4.2006.

To predict evolving GII.4 blockade antibody epitopes, the evolution of the GII.4 noroviruses was assessed over a 36-year period of time by comparing strains from 1974 to 2010. In comparing these sequences, sites of variation in the P2 subdomain were noted, and these sites were mapped onto the crystal structure of the P-domain dimer for the 1997 strain VA387. Surface-exposed sites of variation were then examined to determine which residues may be close enough to constitute a single epitope, and five epitopes were predicted based upon this variation [17, 41].

Epitope A encodes significant amino acid changes over time and has also been demonstrated to be an evolving 011.4 blockade epitope using mouse mAbs [42]. Epitope A is conformational and is located on the top of the capsid proximal to the HBGA binding pocket. Six variable sites were close to each other in the region of this putative epitope, suggesting that these residues may work in concert to change the local structure of Epitope A. The variable, surface-exposed residues include amino acid positions: 294, 296-298, 368 and 372. Epitope A is continuing to evolve in extant strains, whereby the amino acid at position 294 seems to vary extensively in strains from 2008-2010 (amino acid replacements P294A, P294S and P294T have been observed at this position). Epitope B was predicted based upon two variable residues at positions 333 and 382. While these residues are buried in the dimer interface between two chains, the patterns of variation at these sites suggest that they play an important role in the evolution of novel strains, perhaps by evolving replacements that allow the more surface exposed residues in other surface exposed epitopes to dramatically change the physiochemical properties of the amino acid replacements. Residues 340 and 376 make up the variable residues of putative Epitope C. This putative conformation dependent epitope is on the surface and lateral edge of the capsid and is directly proximal to the HBGA binding pocket, suggesting that this epitope may play a role in receptor switching along with Epitope D. Epitope D is comprised of three variable residues from positions 393-395. In the first reported crystal structure for the GII.4 noroviruses, this region was reported to be a secondary HBGA binding site [16]. However, the location of this epitope on the surface of the capsid, directly proximal to the HBGA binding site, suggests that it likely plays a role in both receptor switching and in escape from herd immunity and perhaps both, simultaneously [13, 21, 43, 44]. Epitope D is close enough to the HBGA binding pocket to contribute to or inhibit carbohydrate binding, and yet variable enough to suggest that it is targeted by the immune response. Putative Epitope E is comprised of variable residues 407, 412 and 413, which are surface exposed regions lateral to the HBGA binding pockets and other epitopes. These residues vary with every major epidemic strain after 2002, suggesting that it is a hot spot for the emergence of immunologically novel GII.4 strains. Epitope E is a GII.4.2002 blockade antibody epitope [45]. The fact that this putative epitope is lateral to the HBGA binding pockets suggests that antibodies are targeting regions interior to the capsid surface, which suggests that other epitopes may be present in the P1 subdomain. A few variable residues do not necessarily identify the boundaries of a putative epitope. Moreover, it is nearly impossible to predict the surface area of a putative epitope by sequence analysis alone.

In the studies of this invention, both human and mouse anti-NoV mAbs have been used, coupled with molecular biology approaches to exchange predicted epitopes between GII.4 strain backbones to identify evolving blockade epitopes between GII.4 strains that have circulated from 1987 until 2009. Using this novel approach, three evolving blockade GII.4 antibody epitopes [17, 42, 45] have been identified. Epitope A is comprised of amino acids 294, 296-298, 368 and 372 and is a highly variable blockade epitope that changes with new GII.4 strain emergence. Monoclonal human and mouse antibodies against Epitope A have been described as highly strain selective, lacking reactivity to other GII.4 strains chronologically removed from the immunizing strain. GII.4.2006 and GII.4.2009 were found to differ in reactivity to a human mAb targeting Epitope A, establishing a difference in human neutralizing epitopes between these two strains and supporting escape from herd immunity by antigenic variation at neutralizing epitopes as a mechanism for new NoV strain emergence. Epitope D (residues 393-395) has also been confirmed as an evolving blockade epitope using human anti-NoV mAbs. These findings are particularly interesting as Epitope D has been shown to modulate HBGA binding of GII.4 strains supporting the suggested correlation between epitope escape from herd immunity and altered HBGA binding [13]. Mouse mAbs have confirmed Epitope E (amino acids 407, 412 and 413) as a GII.4.2002 Farmington Hills-specific blockade epitope [45].

Comparing reactivity of polyclonal sera collected from immunized mice and infected humans suggested antigenic variation within the GII.4 noroviruses [13, 35]. The development of mouse mAbs to different time-ordered GII.4 VLPs has greatly facilitated progress towards understanding the complex antigenic relations between these strains by clearly demonstrating antigenic variation over time and epidemic strain [17, 34, 36, 42, 47]. However, to maximally define the mechanistic relationships that exist between antigenic variation, immunity and HBGA binding patterns noted in the GII.4 noroviruses in the context of natural infection history, the cross reactivity patterns, blockade responses, and epitope targets of human anti-GII.4 monoclonal antibodies are needed. Robust approaches exist for the isolation of human monoclonal antibodies that are elicited following virus infection. Using human PBMCs as a source of memory B cells, a panel of human mAbs directed against GII.4 strains was created and used to examine the reactivity of these mAbs to a panel of time-ordered GII.4 VLPs using EIAs and surrogate neutralization assays. We identified one unique, broadly cross reactive antibody that differentially blocks GII.4.1987 through 2009 VLP interactions with carbohydrate ligands, a potential immunotherapeutic for the treatment of acute or chronic GII.4 disease [17]. Unique antibody interactions were also defined with two different surface exposed epitopes that evolve over time. Importantly, antigenic variation in one of these epitopes correlated with changing carbohydrate ligand binding patterns over time, supporting the proposed relationship between epitope escape from human herd immunity and changing HBGA usage for virus docking [13]. In addition to defining the first human monoclonal antibodies with therapeutic potential for treating acute and chronic NoV GII.4 infections, these data support the hypothesis that GII.4 norovirus evolution results in antigenic drift of neutralizing epitopes and consequently, antibody-driven HBGA receptor switching; thus, protective herd immunity is a driving force in norovirus evolution.

EXAMPLE

Identification of Antigenic Epitopes in GII.4 Noroviruses

The evolutionary profile of the epitopes of various human NoV strains is shown in FIG. 1. Table 1 lists several NoV strains of this invention. Five predicted important antigenic epitopes in GII.4 noroviruses were identified. The differences between the epitope amino acid sequences in GII.4-1987 and GII.4-2006 are shown in Table 2. Three of these, epitopes A, D, and E, have been confirmed as GII.4 blockade epitopes. Epitope A is at positions 294, 296-298, 368 and 372, Epitope B is at positions 333 and 382, Epitope C is at positions 340 and 376, epitope D is at positions 393-395 and epitope E is at positions 407, 412 and 413.

To determine if a VLP with blockade epitopes from multiple GII.4 strains could be constructed that could induce a broadly blocking immune response against several strains, mice were immunized with chimeric GII.4 VRPs and the sera were used to test the immune response. GII.4-2006.87A contains the A epitope from 1987 in the 2006 background. GII.4-2006.87A.02E contains the A epitope from 1987 and the E epitope from 2002 in the 2006 background, as shown in FIG. 2.

Mice were immunized with 10 ul ($1\times10^4$) VRPs expressing different parental GII.4 capsids or chimeric GII.4 capsids (FIG. 3). Mice were immunized with VRPs and boosted with the same VRPs on day 21. Seven days post-boost, mice were euthanized and serum was collected to use in ELISA-based assays to determine serum blockade response and reactivity to various VLPs (FIGS. 4A-C).

Figure 4A:
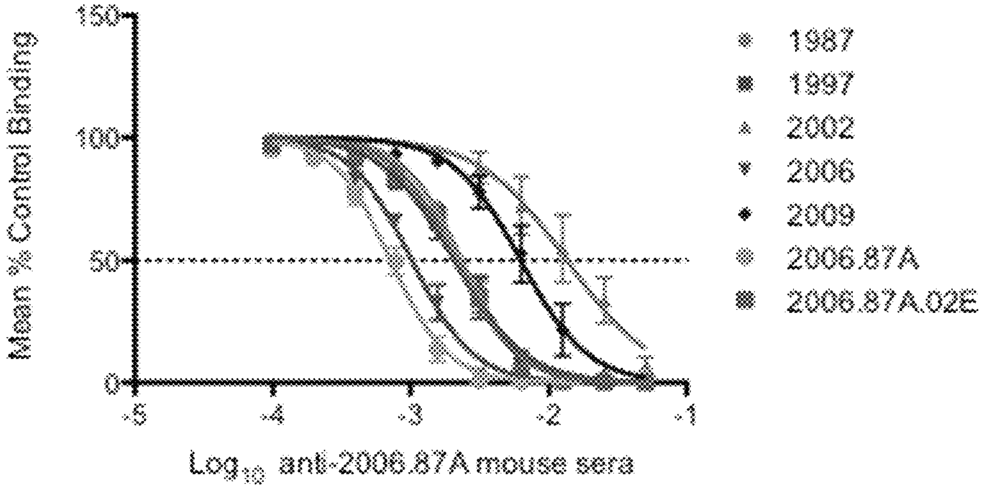
FIG. 4 depicts blockade data with: (A) anti-2006.87A mouse sera; (B) anti-2006.87A.03E mouse polyclonal sera; and (C) anti-2006-87/02/06 mouse polyclonal sera on various VLPs.
Figure 4B:
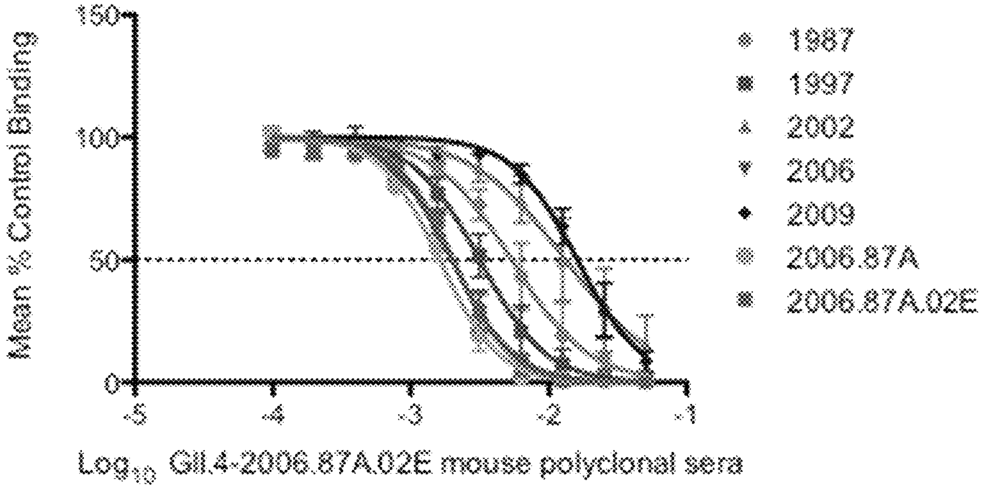
Figure 4C:
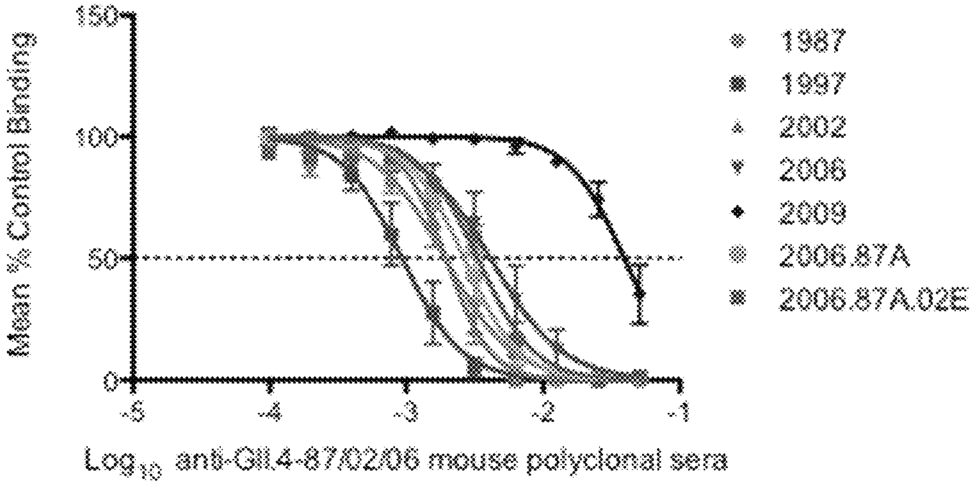
Figure 5A:
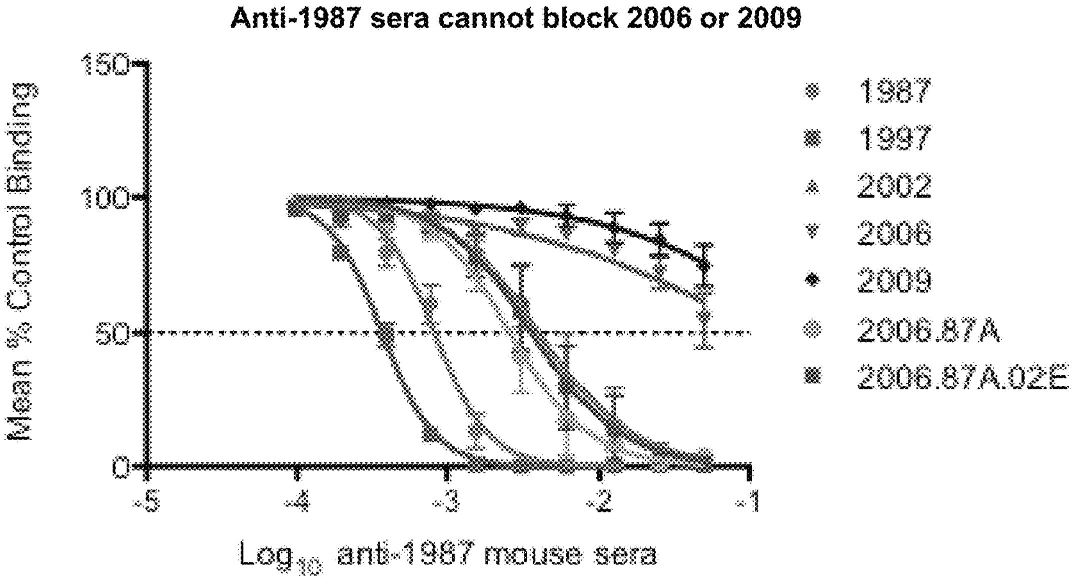
FIG. 5 depicts blockade data with: (A) anti-1987 mouse sera; (B) anti-2002 mouse sera; (C) anti-2006 mouse sera; and (D) anti-2009 mouse sera on various VLPs.
Figure 5B:
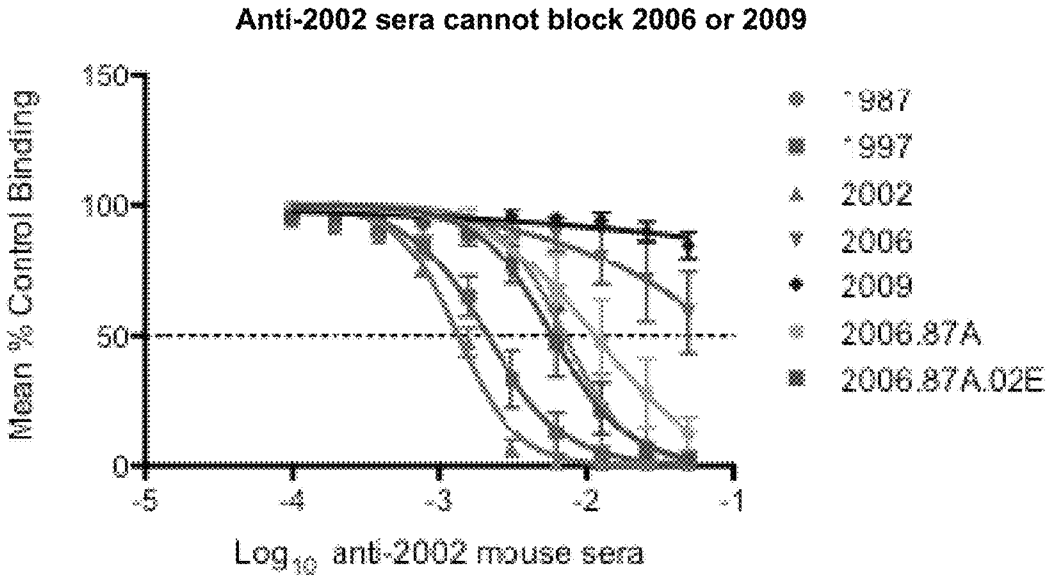
Figure 5C:
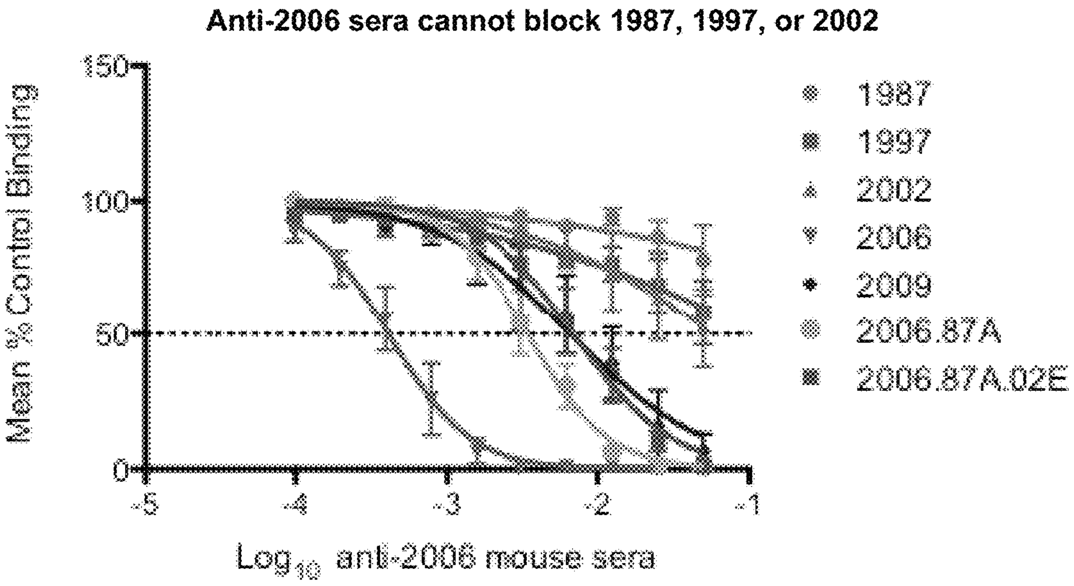
Figure 5D:
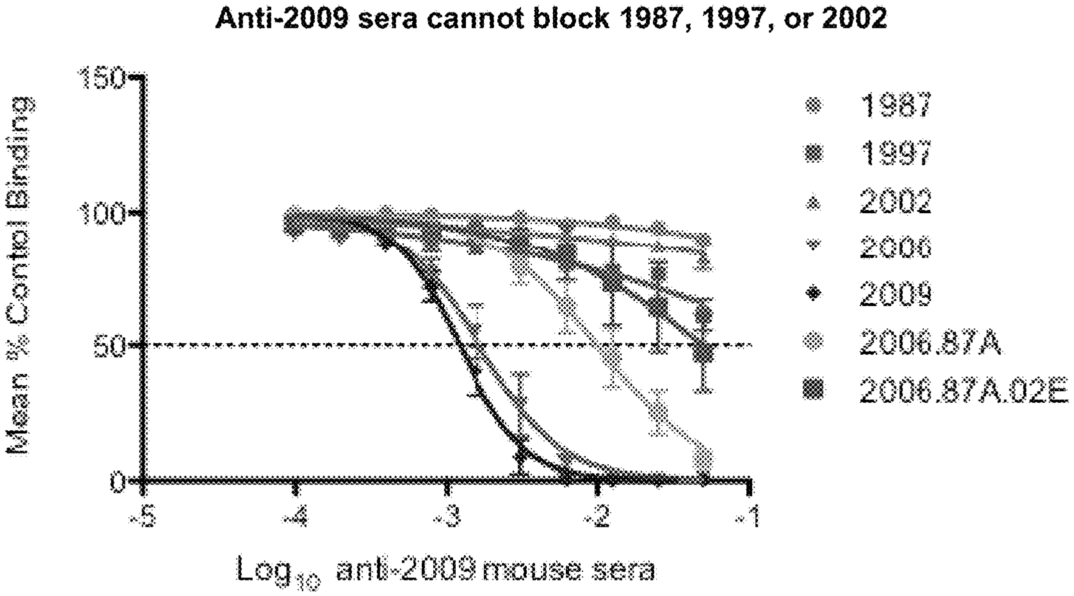

FIGS. 4A-C show sigmoidal curves of the blockade data. The dotted line indicates 50% blockade, the point at which the sera are considered blockade sera. Lines that do not cross the 50% mark indicate the inability of the sera to block that particular VLP. The further left the curve is shifted, the more efficiently the sera blocked that particular VLP. These data indicate that both sera from mice immunized with either chimeric VLP (GII.4-2006.87A, 2006.87A.02E) or a trivalent mix of VLPs (GII.4-1987+2002+2006) are able to block VLPs both included in the chimera/cocktail (1987, 2002, 2006) and those not included (1997, 2009).

Sera from mice immunized with a single parental VLP (GII.4-1987, 2002, 2006, or 2009) were not able to block all of the VLPs tested (FIGS. 5A-D).

Figure 6A:
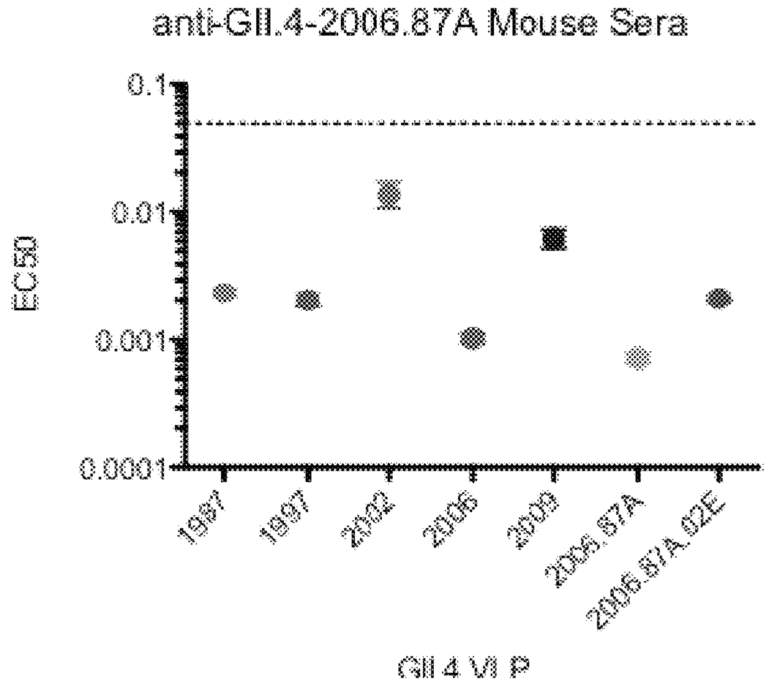
FIG. 6 depicts the $EC_{50}$ at which each sample reaches a blockade response for: (A) anti-GII.4-2006.87A mouse sera; (B) anti-GII.4-2006.87A.02E mouse sera; and (C) anti-GII.4-2006-87/02/06 mouse sera with various VLPs.
Figure 6B:
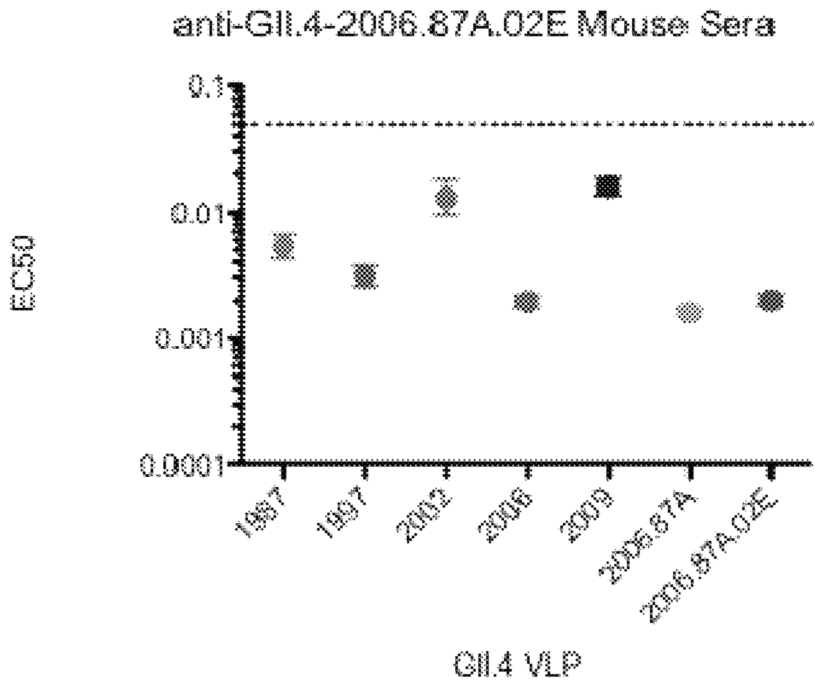
Figure 6C:
Figure 7A:
FIG. 7 depicts the $EC_{50}$ at which each sample reaches a blockade response for: (A) anti-GII.4-1987 mouse sera; (B) anti-GII.4-2002 mouse sera; (C) anti-GII.4-2006 mouse sera; and (D) anti-GII.4-2009 mouse sera with various VLPs.
Figure 7B:
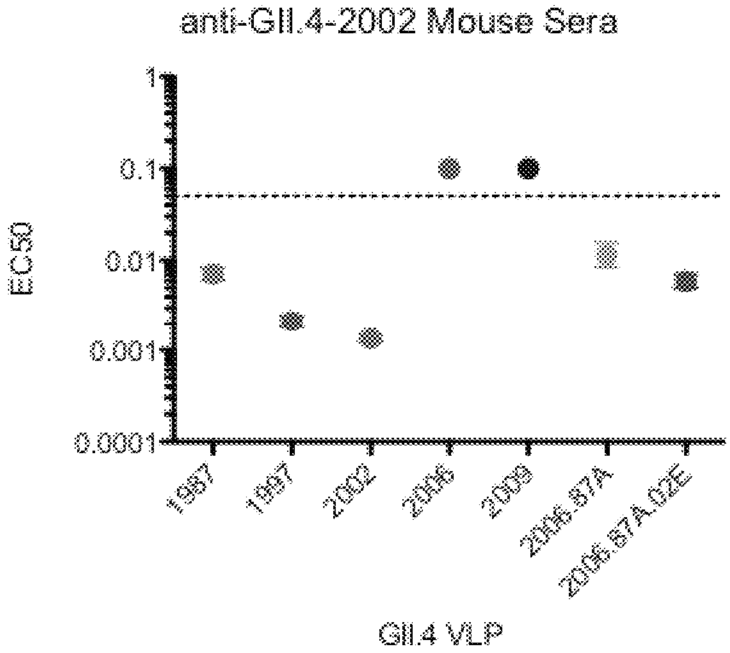
Figure 7C:
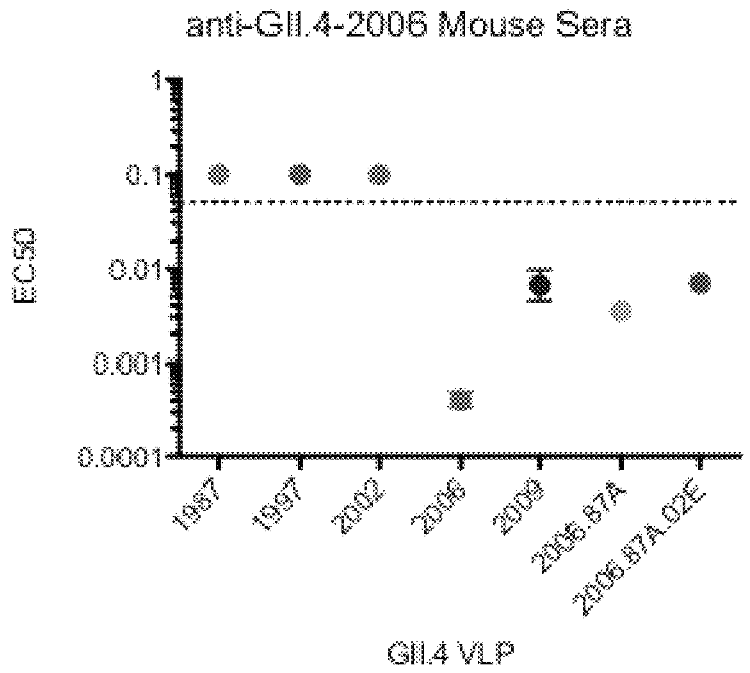
Figure 7D:
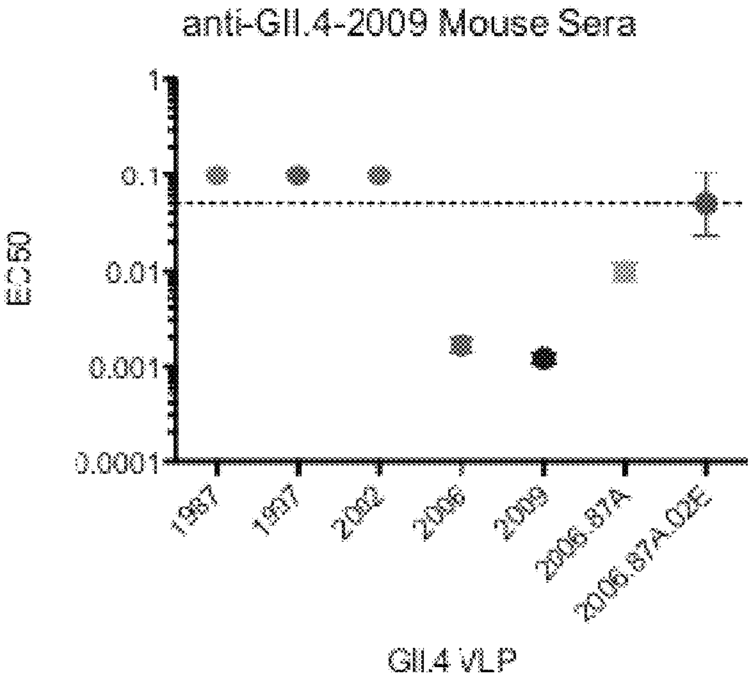

FIGS. 6A-C represent the concentration of serum at which each sample reaches a blockade response (crosses the dotted line in the curve graphs—this is the $EC_{50}$ or 50% blockade). Dots below the line indicate a blockade response for that VLP. The lower the point is on the graph, the better the blockade response of the serum. Sera from mice immunized with either chimera (GII.4-2006.87A, GII.4-2006.87A.02E) or the multivalent 1987+2002+2006 cocktail (GII.4-87/02/06) were able to block all VLPs tested, although to varying degrees. Sera from mice immunized with a single parental strain VLP (GII.4-1987, 2002, 2006, 2009) could not induce a blockade response against all tested strains (FIGS. 7A-D). Dots above the line indicate a VLP that was not blocked even at the highest serum concentration tested (5%).

Table 3 depicts a summary of blockade responses of parental, chimeric and multivalent sera. These data show that monovalent VLP vaccines designed after strains circulating between 1987-2009 (GII.4) elicit poor cross protection to related strains. Multivalent vaccines (multiple VLPs, or multiple VRPs encoding different NoV VLP) give broader responses. Importantly, a VLP has been designed with one or multiple time-ordered GII.4 epitopes that elicited a broadly neutralizing antibody response that captured more unique strains.

Figure 8:
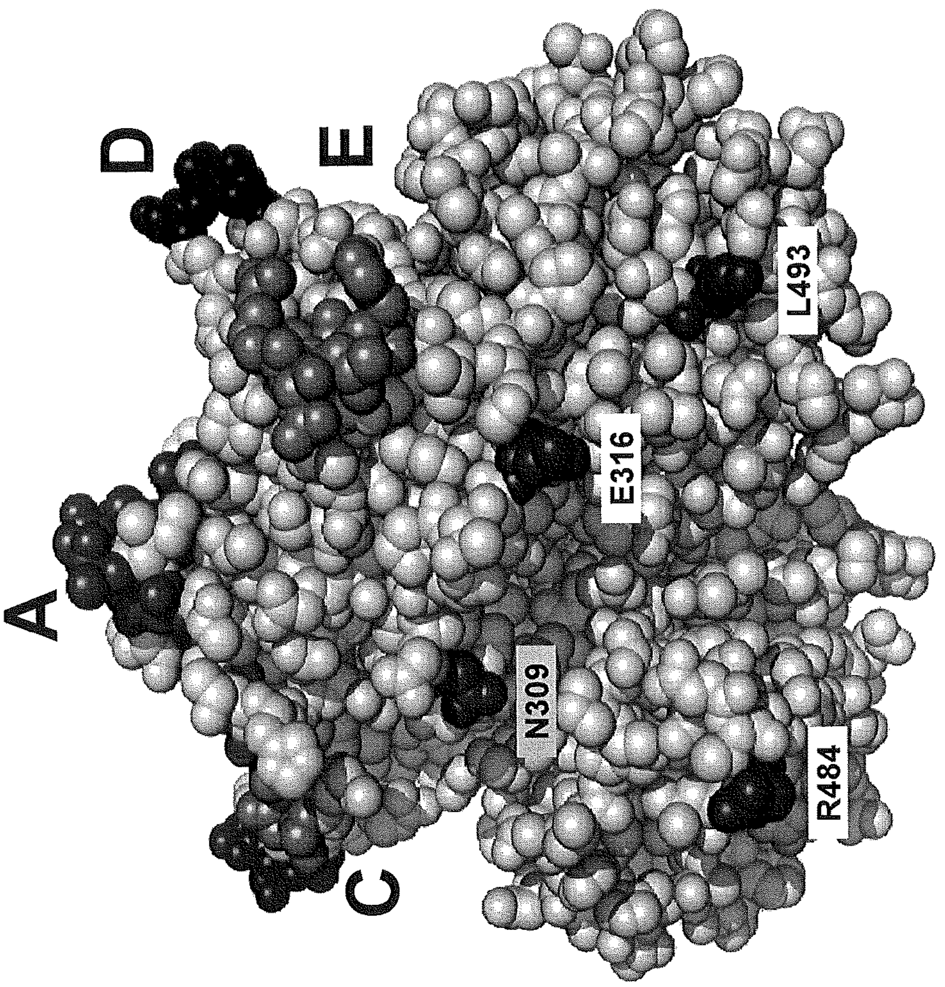
FIG. 8 depicts the structural model of a predicted conserved GII.4 norovirus blockade epitope.

Identification of a GII.4 Norovirus Conserved Blockade Epitope Using Human Monoclonal Antibodies The structural model of predicted conserved GII.4 norovirus blockade epitopes is shown in FIG. 8. Epitopes A, D and E are confirmed GII.4 evolving blockade antibody epitopes. Epitope C is a predicted GII.4 evolving blockade antibody epitope. Residues R484, N309, E316, L493 comprise a predicted GII.4 conserved blockade antibody epitope (Epitope F) which is present in all GII.4 strains tested to date. Note that this epitope lies on the side of the P domain underneath the E epitope.

Figure 9:
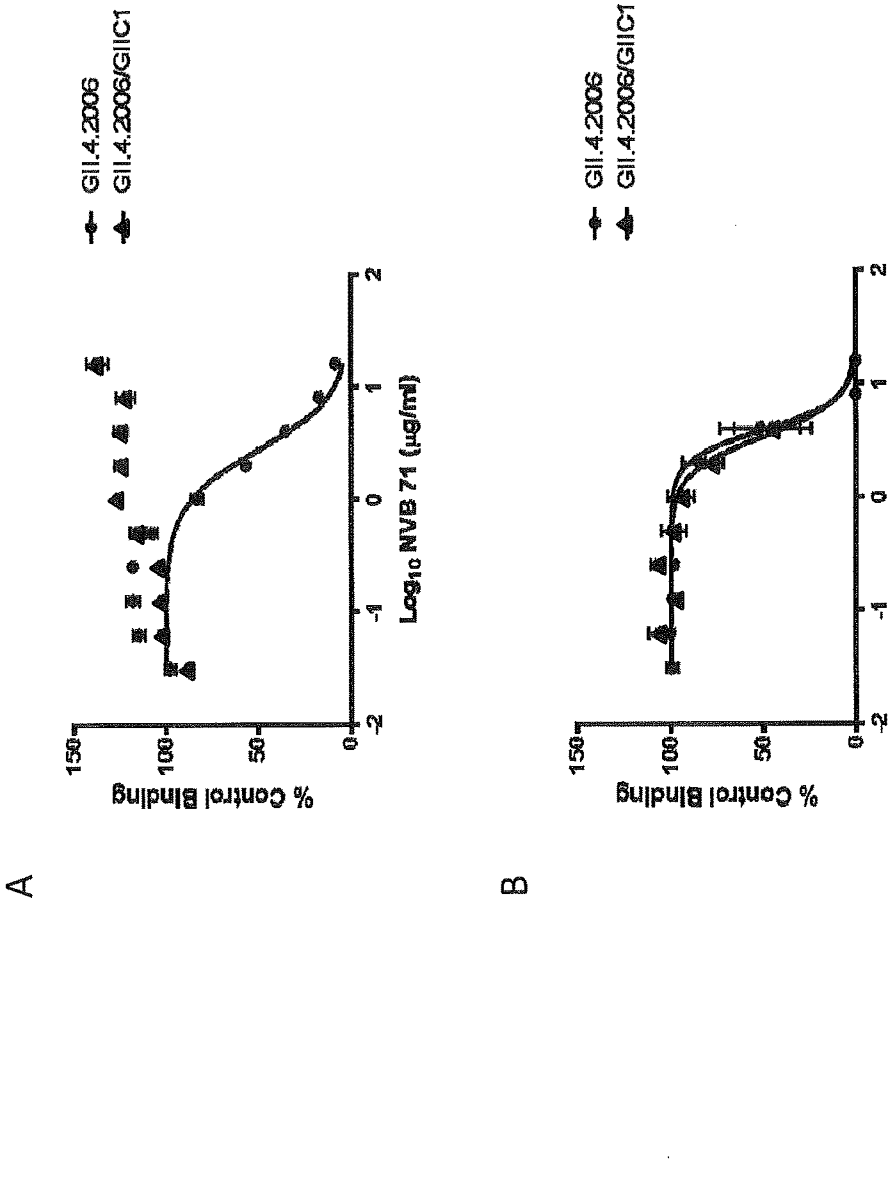
FIG. 9 depicts the identification of a GII.4 norovirus conserved blockade epitope using human monoclonal antibodies.

The identification of a GII.4 norovirus conserved blockade epitope using human monoclonal antibodies is shown in FIG. 9. Monoclonal antibodies were assayed for ability to block VLP interaction with carbohydrate ligand. Sigmoidal curves were fit to the mean percent control binding (percent of VLP bound to PGM in the presence of antibody pretreatment compared to the amount of VLP bound in the absence of antibody pretreatment). Error bars represent SEM. GII.4.2006 VLPs were constructed with mutations in the predicted epitope and the impact on binding of human anti-GII.4 monoclonal antibodies was tested. FIG. 9A shows NVB71 blocked binding of the parent GII.4.2006 VLP.

Amino acid changes in the predicted GII.4 conserved blockade antibody epitope (GII.4.2006.GIIC1) ablated blockade potential of this antibody, identifying amino acids R484, E316, L493 as the binding site of NVB71 and as a conserved GII.4 blockade epitope. FIG. 9B shows changes in amino acids R484, E316, L493 have no effect on blockade of an antibody to GII.4.2006 Epitope A (NVB43.9).

The foregoing is illustrative of the present invention, and is not to be construed as limiting thereof.

REFERENCES

1. *Updated norovirus outbreak management and disease prevention guidelines*. MMWR Recomm Rep, 2011. 60(RR-3): p. 1-18.
2. Hutson, A. M., R. L. Atmar, and M. K. Estes, *Norovirus disease: changing epidemiology and host susceptibility factors*. Trends Microbiol, 2004. 12(6): p. 279-87.
3. Estes, M. K., B. V. Prasad, and R. L. Atmar, *Noroviruses everywhere: has something changed?* Curr Opin Infect Dis, 2006. 19(5): p. 467-74.
4. Koopmans, M., et al., *Molecular epidemiology of human enteric caliciviruses in The Netherlands*. J Infect Dis, 2000. 181 Suppl 2: p. S262-9.
5. *Norovirus activity—United States,* 2006-2007. MMWR Morb Mortal Wkly Rep, 2007. 56(33): p. 842-6.
6. Okada, M., et al., *Genetic analysis of noroviruses associated with fatalities in healthcare facilities*. Arch Virol, 2006. 151(8): p. 1635-41.
7. Harris, J. P., et al., *Deaths from norovirus among the elderly, England and Wales*. Emerg Infect Dis, 2008. 14(10): p. 1546-52.
8. Schorn, R., et al., *Chronic norovirus infection after kidney transplantation: molecular evidence for immune-driven viral evolution*, Clin Infect Dis, 2010. 51(3): p. 307-14.
9. Patel, M. M., et al., *Systematic literature review of role of noroviruses in sporadic gastroenteritis*. Emerg Infect Dis, 2008. 14(8): p. 1224-31.
10. Atmar, R. L., et al., *Norovirus vaccine against experimental human Norwalk Virus illness*. N Engl J Med, 2011. 365(23): p. 2178-87.
11. Prasad, B. V., et al., *X-ray crystallographic structure of the Norwalk virus capsid*. Science, 1999. 286(5438): p. 287-90.
12. Zheng, D. P., et al., *Norovirus classification and proposed strain nomenclature*. Virology, 2006. 346(2): p. 312-23.
13. Lindesmith, L. C., et al., *Mechanisms of GII.*4 *norovirus persistence in human populations*. PLoS Med, 2008. 5(2): p. e31.
14. Chen, R., et al., *X-ray structure of a native calicivirus: structural insights into antigenic diversity and host specificity*. Proc Natl Acad Sci USA, 2006. 103(21): p. 8048-53.
15. Lochridge, V. P., et al., *Epitopes in the P*2 *domain of norovirus VP*1 *recognized by monoclonal antibodies that block cell interactions*. J Gen Virol, 2005. 86(Pt 10): p. 2799-806.
16. Cao, S., et al., *Structural Basis for the Recognition of Blood Group Trisaccharides by Norovirus*. J Virol, 2007. 81(11): p. 549-57.
17. Lindesmith, L. C., et al., *Immunogenetic Mechanisms Driving Norovirus GII.*4 *Antigenic Variation*. PLoS Pathog, 2012. 8(5): p. e1002705 (incorporated by reference herein from U.S. Provisional Application Ser. No. 61/798,946)
18. Siebenga, J. J., et al., *Epochal Evolution of GGII.*4 *Norovirus Capsid Proteins from* 1995 *to* 2006. J Virol, 2007. 81(18): p. 9932-41.
19. Bull, R. A., et al., *Rapid evolution of pandemic noroviruses of the GII.*4 *lineage*. PLoS Pathog, 2010. 6(3): p. e1000831.
20. Bok, K., et al., *Evolutionary dynamics of GII.*4 *noroviruses over a* 34-*year period*. J Virol, 2009. 83(22): p. 11890-901.
21. Shanker, S., et al., *Structural Analysis of HBGA Binding Specificity in a Norovirus GII.*4 *Epidemic Variant: Implications for Epochal Evolution. Journal of Virology,* 2011. 85(17): p. 8635-45.
22. Allen, D. J., et al., *Analysis of amino acid variation in the P*2 *domain of the GII-*4 *norovirus VP*1 *protein reveals putative variant-specific epitopes*. PLoS ONE, 2008. 3(1): p. e1485.
23. de Rougemont, A., et al., *Qualitative and quantitative analysis of the binding of GII.*4 *norovirus variants onto human blood group antigens*. Journal of Virology., 2011. 85(9): p. 4057-70.
24. Noel, J. S., et al., *Identification of a distinct common strain of "Norwalk-like viruses" having a global distribution*. J Infect Dis, 1999. 179(6): p. 1334-44.
25. Vinje, J., S. Altena, and M. Koopmans, *The incidence and genetic variability of small round-structured viruses in outbreaks of gastroenteritis in the Netherlands*. J Infect Dis, 1997. 176: p. 1374-1378.
26. Widdowson, M. A., et al., *Outbreaks of acute gastroenteritis on cruise ships and on land: identification of a predominant circulating strain of norovirus—United States,* 2002. J Infect Dis, 2004. 190(1): p. 27-36.
27. Fankhauser, R. L., et al., *Epidemiologic and molecular trends of "Norwalk-like viruses" associated with outbreaks of gastroenteritis in the United States*. J Infect Dis, 2002. 186(1): p. 1-7.
28. Bull, R. A., et al., *Emergence of a new norovirus genotype II.*4 *variant associated with global outbreaks of gastroenteritis*. J Clin Microbiol, 2006. 44(2): p. 327-33.
29. Kroneman, A., et al., *Increase in norovirus activity reported in Europe*. Euro Surveill, 2006. 11(12): p. E061214 1.
30. Phan, T. G., et al., *Changing distribution of norovirus genotypes and genetic analysis of recombinant GIIb among infants and children with diarrhea in Japan*. J Med Virol, 2006. 78(7): p. 971-8.
31. Siebenga, J., et al., *Food-borne viruses in Europe network report: the norovirus GII.*4 2006*b* (*for US named Minerva-like, for Japan Kobe*034-*like, for UK V*6) variant now dominant in early seasonal surveillance, Euro Surveill, 2008. 13(2).
32. Vega E, B. L., Gregoricus N, Williams K, Lee D, VinjéJ., *Novel surveillance network for norovirus gastroenteritis outbreaks, United States*, Emerg Infect Dis., 2011. 17(8): p. 1389-95.
33. Prevention, C.f.D.C.a., *Notes from the Field: Emergence of New Norovirus Strain GII.*4 *Sydney—United States,* 2012. MMWR Morb Mortal Wkly Rep, 2013. 62: p. 55.
34. Lindesmith, L. C., et al., *Emergence of a Norovirus GII.*4 *Strain Correlates with Changes in Evolving Blockade Epitopes*. Journal of Virology., 2013. 87(5): p. 2803-13. (incorporated by reference herein from U.S. Provisional Application Ser. No. 61/798,946)
35. Cannon, J. L., et al., *Herd immunity to GII.*4 *noroviruses is supported by outbreak patient sera*. J Virol, 2009. 83(11): p. 5363-74.

36. Lindesmith, L. C., E. F. Donaldson, and R. S. Baric, *Norovirus GII.4 strain antigenic variation*. Journal of Virology., 2011. 85(1): p. 231-42.
37. Harrington, P. R., et al., *Binding of Norwalk virus-like particles to ABH histo-blood group antigens is blocked by antisera from infected human volunteers or experimentally vaccinated mice*. J Virol, 2002. 76(23): p. 12335-43.
38. Lindesmith, L. C., et al., *Heterotypic humoral and cellular immune responses following Norwalk virus infection*. Journal of Virology., 2010. 84(4): p. 1800-15.
39. Bok, K., et al., *Chimpanzees as an animal model for human norovirus infection and vaccine development*. Proc Natl Acad Sci USA, 2011. 108(1): p. 325-30.
40. Reeck, A., et al., *Serological Correlate of Protection against Norovirus-Induced Gastroenteritis*. The Journal of Infectious Diseases, 2010. 202(8): p. 1212-8.
41. Donaldson, E. F., et al., *Viral shape-shifting: norovirus evasion of the human immune system*. Nat Rev Microbiol, 2010. 8(3): p. 231-41.
42. Debbink, K., et al., *Genetic mapping of a highly variable norovirus GII.4 blockade epitope: potential role in escape from human herd immunity*. Journal of Virology., 2012. 86(2): p. 1214-26. (incorporated by reference herein from U.S. Provisional Application Ser. No. 61/798,946)
43. Donaldson, E. F., et al., *Norovirus pathogenesis: mechanisms of persistence and immune evasion in human populations*. Immunol Rev, 2008. 225: p. 190-211.
44. Debbink, K., et al., *Genetic Mapping of a Highly Variable Norovirus GII.4 Blockade Epitope: Potential Role in Contribution in Escape from Human Herd Immunity*. Journal of Virology., 2011. 86(2): p. 1214-1226.
45. Lindesmith, L. C., et al., *Monoclonal antibody-based antigenic mapping of norovirus GII.4-2002*. Journal of virology., 2012. 86(2): p. 873-83. (incorporated by reference herein from U.S. Provisional Application Ser. No. 61/798,946)
46. Siebenga, J. J., et al., *Phylodynamic reconstruction reveals norovirus GII.4 epidemic expansions and their molecular determinants*. PLoS Pathog, 2010. 6(5): p. e1000884.
47. Allen, D. J., et al., *Characterisation of a GII-4 norovirus variant-specific surface-exposed site involved in antibody binding*. Virol J, 2009. 6: p. 150.
48. Zakikhany, K., et al., *Molecular Evolution of GII-4 Norovirus Strains*. PLoS ONE, 2012. 7(7): p. e41625.

TABLE 1

NoV strains

| VLP | Pandemic Cluster | GenBank Access. No. | Original Strain | SEQ ID NO |
|---|---|---|---|---|
| GII.4.1974 | | ACT76139.1 | | 1 |
| GII.4.1987 | Ancestral | AAK50355.1 | Hu/NLV/GII/MD14512/1987/US | 2 |
| GII.4.1997 | US95/96 | AFJ04707.1 | Outbreak Isolate | 3 |
| GII.4.2002 | Farmington Hills | AFJ04708.1 | Outbreak Isolate | 4 |
| GII.4.2002a | | n/a | | 5 |
| GII.4.2004 | Hunter | AAZ31376.2 | Hu/GII.4/Hunter284E/04O/AU | 6 |
| GII.4.2005 | None | BAE98194.1 | Hu/Sakai/04/179/2005/JP | 7 |
| GII.4.2006 | Minerva/2006b | AFJ04709.1 | Outbreak Isolate | 8 |
| GII.4.2007 | | AB46912.1 | Hu/GII.4/cruiseship/2007/ZAF | 9 |
| GII.4.2008a | | ACX31885.1 | Hu/GII.4/NSW390I/AU | 10 |
| GII.4.2008s | | BAH30707.1 | Hu/GII.4/Stockholm/19865/SE | 11 |
| GII.4.2009 | Minerva/2006b | ADD10375.1 | Hu/GII.4/New_Orleans1805/2009/USA | 12 |
| GII.4.2012 | Sydney | AFV08795.1 | Hu/GII.4/Sydney/NSW0514/2012/AU | 13 |

TABLE 2

GII.4-1987 and GII.4-2006 epitope differences.

| Amino acid residue* | 280 | 285 | 294 | 296 | 297 | 298 | 306 | 309 | 333 | 339 | 340 | 346 | 352 |
|---|---|---|---|---|---|---|---|---|---|---|---|---|---|
| GII.4-1987# | A | N | V | S | H | D | Q | S | L | R | A | A | S |
| GII.4-2006 | P | T | A | S | R | N | L | N | V | K | G | G | Y |
| **Amino acid residue*** | **356** | **357** | **368** | **372** | **376** | **378** | **393** | **394** | **395** | **397** | **407** | **412** | **413** |
| GII.4-1987# | V | H | T | N | Q | G | D | — | H | Q | N | T | G |
| GII.4-2006 | A | P | S | E | E | H | S | T | T | R | S | N | V |

*Amino acid 382 is K for both GII.4-1987 and GII.4-2006
#Epitope E for GII.4-1987 is at amino acid positions 406, 411 and 412

TABLE 3

Blockade responses of parental, chimeric and multivalent sera.

| | | GII.4-VLP | | | | | | |
|---|---|---|---|---|---|---|---|---|
| Serum Blockade Responses | | 1987 | 1997 | 2002 | 2006 | 2009 | 2006.87A | 2006.87A.02E |
| Sera | anti-GII.4-1987 | yes | yes | yes | no | no | yes | yes |
| | anti-GII.4-2002 | yes | yes | yes | no | no | yes | yes |
| | anti-GII.4-2006 | no | no | no | yes | yes | yes | yes |

TABLE 3-continued

Blockade responses of parental, chimeric and multivalent sera.

| Serum Blockade Responses | GII.4-VLP 1987 | 1997 | 2002 | 2006 | 2009 | 2006.87A | 2006.87A.02E |
|---|---|---|---|---|---|---|---|
| anti-GII.4-2009 | no | no | no | yes | yes | yes | yes |
| anti-GII.4-2006.87A | yes | yes | yes | yes | yes | yes | yes |
| anti-GII.4-2006.87A.02E | yes | yes | yes | yes | yes | yes | yes |
| anti-GII.4.87/02/06 | yes | yes | yes | yes | yes | yes | yes |

That which is claimed is:

1. A chimeric norovirus capsid protein consisting of a norovirus VP1 major capsid protein backbone from norovirus strain GII.4.1974 (SEQ ID NO:14), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more, in any combination, of the following sets of amino acid residues (a)-(i):

a) amino acid residues 294, 296, 297, 298, 368 and 372 (Epitope A);
b) amino acid residues 333 and 382 (Epitope B);
c) amino acid residues 340 and 376 (Epitope C);
d) amino acid residues 393, 394 and 395 (Epitope D);
e) amino acid residues 407, 412 and 413 (Epitope E); and
f) amino acid residues 310, 316, 484 and 493 (Epitope F), wherein amino acid residue numbering of (a)-(f) is based on the amino acid sequence of any of SEQ ID NOs:4-13; and
g) amino acid residues 393 and 394 (Epitope D);
h) amino acid residues 406, 411 and 412 (Epitope E); and
i) amino acid residues 310, 316, 483 and 492 (Epitope F), wherein amino acid residue numbering of (g)-(i) is based on the amino acid sequence of SEQ ID NOs:2, 3 or 14, are substituted into the capsid protein backbone to introduce at least one epitope from each of two or more different norovirus strains of the above norovirus strains, each of which is different from one another and each of which is different from the norovirus strain of the capsid protein backbone.

2. A synthetic backbone molecule comprising two or more sets of amino acid residues wherein each set of amino acid residues forms a norovirus conformational epitope, wherein the two or more sets of amino acid residues each form a conformational epitope from two or more norovirus strains that are different from one another and wherein the two or more sets of amino acid residues are selected in any combination from the group consisting of the following sets of amino acid residues (a)-(i):

a) amino acid residues 294, 296, 297, 298, 368 and 372 (Epitope A);

b) amino acid residues 333 and 382 (Epitope B);

c) amino acid residues 340 and 376 (Epitope C);

d) amino acid residues 393, 394 and 395 (Epitope D);

e) amino acid residues 407, 412 and 413 (Epitope E); and f) amino acid residues 310, 316, 484 and 493 (Epitope F), wherein amino acid residue numbering of (a)-(f) is based on the amino acid sequence of any of SEQ ID NOs:4-13; and g) amino acid residues 393 and 394 (Epitope D);

h) amino acid residues 406, 411 and 412 (Epitope E); and i) amino acid residues 310, 316, 483 and 492 (Epitope F), wherein amino acid residue numbering of (g)-(i) is based on the amino acid sequence of SEQ ID NOs:2, 3 or 14, from two or more norovirus strains that are different from one another, wherein the synthetic backbone molecule allows for formation of two or more norovirus conformational epitopes, and wherein the synthetic backbone molecule is not a norovirus capsid protein.

3. A norovirus P particle consisting of multiple copies of a norovirus P domain backbone from norovirus strain GII.4.1974 (SEQ ID NO:14), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more, in any combination, of the following sets of amino acid residues (a)-(i):

a) amino acid residues 294, 296, 297, 298, 368 and 372 (Epitope A);

b) amino acid residues 333 and 382 (Epitope B);

c) amino acid residues 340 and 376 (Epitope C);

d) amino acid residues 393, 394 and 395 (Epitope D);

e) amino acid residues 407, 412 and 413 (Epitope E); and f) amino acid residues 310, 316, 484 and 493 (Epitope F), wherein amino acid residue numbering of (a)-(f) is based on the amino acid sequence of any of SEQ ID NOs:4-13; and g) amino acid residues 393 and 394 (Epitope D);

h) amino acid residues 406, 411 and 412 (Epitope E); and i) amino acid residues 310, 316, 483 and 492 (Epitope F), wherein amino acid residue numbering of (g)-(i) is based on the amino acid sequence of SEQ ID NOs:2, 3 or 14, are substituted into the P domain backbone to introduce at least one epitope from each of two or more norovirus strains of the above norovirus strains, each of which is different from one another and each of which is different from the norovirus strain of the P domain backbone, wherein the epitopes are presented on the P particle surface.

4. The chimeric norovirus capsid protein of claim 1, wherein the norovirus VP1 major capsid protein backbone is from GII.4.2006.

5. The chimeric norovirus capsid protein of claim 4, comprising Epitope A from GII.4.1987 and Epitope E from GII.4.2002.

6. A virus like particle (VLP) comprising the chimeric norovirus capsid protein of claim 1.

7. A composition comprising the chimeric norovirus capsid protein of claim 1 in a pharmaceutically acceptable carrier.

8. A method of producing an immune response to a norovirus in a subject, comprising administering to the subject an effective amount of the chimeric norovirus capsid protein of claim 1.

* * * * *

UNITED STATES PATENT AND TRADEMARK OFFICE

CERTIFICATE OF CORRECTION

PATENT NO. : 9,975,923 B2
APPLICATION NO. : 14/213469
DATED : May 22, 2018
INVENTOR(S) : Baric et al.

It is certified that error appears in the above-identified patent and that said Letters Patent is hereby corrected as shown below:

In the Specification

Column 4, Line 26: Please correct “OENBANK” to read -- GENBANK --

Column 4, Line 41: Please correct “NO:4” to read -- NO:14 --

Column 6, Line 21: Please correct “ftvspmapgeil” to read -- ftvsprnapgeil --

Column 6, Line 24: Please correct “ksftypilt” to read -- ksftvpilt --

Column 6, Line 25: Please correct “vqpqngratd” to read -- vqpqngrcttd --

Column 9, Line 9: Please correct “011.4-2005” to read -- GII.4-2005 --

Column 19, Line 34: Please correct “ETA” to read -- EIA --

Column 19, Line 39: Please correct “011.4” to read -- GII.4 --

Column 19, Line 44: Please correct “011.4.1987” to read -- GII.4.1987 --

Column 19, Line 60: Please correct “011.4” to read -- GII.4 --

Signed and Sealed this
Fourth Day of September, 2018

Andrei Iancu
*Director of the United States Patent and Trademark Office*